United States Patent
Rubin et al.

(10) Patent No.: US 11,450,433 B2
(45) Date of Patent: Sep. 20, 2022

(54) SYSTEM AND METHOD FOR REMOTE DIAGNOSIS OF DISEASE PROGRESSION

(71) Applicant: BeCare Link LLC, Rumson, NJ (US)

(72) Inventors: Lawrence D. Rubin, Rumson, NJ (US); David Putrino, Brooklyn, NY (US); Timothy Vartanian, Brookline, MA (US)

(73) Assignee: Becare Link, LLC, Rumson, NJ (US)

( * ) Notice: Subject to any disclaimer, the term of this patent is extended or adjusted under 35 U.S.C. 154(b) by 536 days.

(21) Appl. No.: 15/885,938

(22) Filed: Feb. 1, 2018

(65) Prior Publication Data

US 2018/0218791 A1 Aug. 2, 2018

Related U.S. Application Data

(60) Provisional application No. 62/453,793, filed on Feb. 2, 2017.

(51) Int. Cl.

| | |
|---|---|
| *G16H 50/20* | (2018.01) |
| *G16H 80/00* | (2018.01) |
| *G16H 40/67* | (2018.01) |
| *G16H 50/30* | (2018.01) |
| *G16H 20/30* | (2018.01) |

(52) U.S. Cl.
CPC ............ *G16H 50/20* (2018.01); *G16H 20/30* (2018.01); *G16H 40/67* (2018.01); *G16H 50/30* (2018.01); *G16H 80/00* (2018.01)

(58) Field of Classification Search
CPC ....... A61B 5/11; A61B 5/7275; A61B 5/0525; A61B 5/165; A61B 5/4082; A61B 5/7264; A61B 5/369; G01N 33/564; G06T 15/00; G06F 19/3418; G06F 19/322; H04W 4/04; A61C 5/4064; G07C 1/12

USPC ............... 600/595, 300, 301, 544; 436/128; 345/419; 455/416; 705/3; 702/177

See application file for complete search history.

(56) References Cited

U.S. PATENT DOCUMENTS 8,568,311 B2 * 10/2013 LaPlaca ................... G09B 7/00
600/301
8,764,651 B2 * 7/2014 Tran ....................... A61B 5/1114
600/300

(Continued)

FOREIGN PATENT DOCUMENTS

CN 109002201 A * 12/2018 ............. G06F 3/041
WO 2016038516 A3 3/2016

OTHER PUBLICATIONS

Google patents search, May 11, 2020 (Year: 2020).*

(Continued)

*Primary Examiner* — Dilek B Cobanoglu
(74) *Attorney, Agent, or Firm* — Gregory J. Winsky, Esq.; Archer & Greiner, P.C.

(57) ABSTRACT

A system and method based on the use of a mobile application running on a handheld mobile device that can be manipulated by a user/patient with the result that the data gathered by the application is communicated via a secure link to a computer service in order for evaluation of the user/patient's neurological and physical functioning for purposes of detecting changes in the progression of certain functions to aid in the diagnosis of certain diseases, such as multiple sclerosis and related neurological diseases.

2 Claims, 43 Drawing Sheets

(56) References Cited

U.S. PATENT DOCUMENTS

| | | | | |
|---|---|---|---|---|
| 8,945,935 B2* | 2/2015 | Haick | ................... | B82Y 15/00 |
| | | | | 436/127 |
| 9,020,476 B2* | 4/2015 | Leipzig | ............... | H04L 41/5064 |
| | | | | 455/416 |
| 9,445,769 B2* | 9/2016 | Ghassemzadeh | ........ | A43B 3/34 |
| 2007/0143071 A1* | 6/2007 | Delargy | ................... | G07C 1/12 |
| | | | | 702/177 |
| 2009/0018407 A1* | 1/2009 | Jung | ...................... | G16H 40/67 |
| | | | | 600/301 |
| 2009/0264785 A1* | 10/2009 | Causevic | ............... | A61B 5/369 |
| | | | | 600/544 |
| 2010/0169409 A1 | 7/2010 | Fallon et al. | | |
| 2010/0280579 A1 | 10/2010 | Denison et al. | | |
| 2011/0054361 A1* | 3/2011 | Sakoda | ................ | A61B 5/4082 |
| | | | | 600/595 |
| 2012/0127157 A1* | 5/2012 | Adler | ..................... | G06Q 10/00 |
| | | | | 345/419 |
| 2013/0041290 A1* | 2/2013 | Kording | ................. | A61B 5/117 |
| | | | | 600/595 |
| 2014/0100486 A1 | 4/2014 | Alberts | | |
| 2014/0163426 A1 | 6/2014 | Alberts | | |
| 2014/0278536 A1* | 9/2014 | Zhang | ................... | G16H 40/67 |
| | | | | 705/3 |
| 2015/0018630 A1* | 1/2015 | Fotuhi | ................. | A61B 5/4064 |
| | | | | 600/300 |
| 2015/0154281 A1 | 6/2015 | Carlsson et al. | | |
| 2016/0022193 A1* | 1/2016 | Rau | ........................ | A61B 5/165 |
| | | | | 600/301 |
| 2016/0317077 A1 | 11/2016 | Sillay | | |
| 2017/0124276 A1* | 5/2017 | Tee | .................... | G08B 21/0453 |
| 2017/0344706 A1* | 11/2017 | Torres | .................. | A61B 5/7264 |

OTHER PUBLICATIONS

Google patents search, Dec. 10, 2021 (Year: 2021).*
Google patents search, Feb. 26, 2022 (Year: 2022).*
Ip.com search, Feb. 26, 2022 (Year: 2022).*
Tracking the Evolution of Smartphone Sensing for Monitoring Human Movement, Michael B. del Rosario, Stephen J. Redmond † and Nigel H. Lovell, Graduate School of Biomedical Engineering, UNSW Australia, Sydney, Sensors 2015, 15, Published: Jul. 31, 2015 (Year: 2015).*
Ip.com search, May 23, 2022 (Year: 2022).*
Journal of the Neurological Sciences, Motor assessment of upper extremity function and its relation with fatigue, cognitive function and quality of life in multiple sclerosis patients, Nuray Yozbatiran, School of Physical Therapy and Rehabilitation, Dokuz Eylul University, May 5, 2006 (Year: 2006).*
Google Scholar search, Jun. 27, 2022 (Year: 2022).*
Remote Smartphone Monitoring for Management of Parkinson's Disease, Teresa H. Sanders, MS * Georgia Institute of Technology , Mar. 29-31, 2013 (Year: 2013).*

* cited by examiner

SYSTEM AND METHOD FOR REMOTE DIAGNOSIS OF DISEASE PROGRESSION

CROSS REFERENCE TO RELATED APPLICATION

This application claims the benefit of U.S. Provisional Application No. 62/326,295 filed on Feb. 2, 2017.

FIELD OF INVENTION

The present invention relates to a mobile application that communicates with a remote computer service that can be used by physicians to evaluate a patient's neurological and physical functioning for purposes of detecting changes in the progression of certain functions to aid in the diagnosis of certain diseases, such as multiple sclerosis and related neurological diseases.

BACKGROUND

Multiple sclerosis ("MS") is a chronic and often disabling disease that has been linked to a wide range of symptoms. Traditionally, MS related symptoms have been evaluated using the current gold-standard, the Kurtzke Expanded Disability Status Scale (EDSS), along with other outcome measures, referred to herein as the "Functional Tests." These Functional Tests measure disability and progression of disability in patients with MS. Recently, the Timed Up and Go (or "TUG") Test, along with other tests have emerged as clinically relevant tests for measuring how well an individual can move around in their environment and participate in the activities of daily living. Dr. John Kurtzke developed the Kurtzke Disability Status Scale ("DSS") in the 1950s to measure the disability status of people with multiple sclerosis in order to create a standardized way for health care providers to quantify the level of functioning in patients that were diagnosed with MS. TheExpanded Disability Status Scale (EDSS) is widely used and is accepted as a valid tool to clinically measure and evaluate MS patients' level of functioning.

The EDSS provides a total score on a scale that ranges from 0 to 10. The first levels 1.0 to 4.5 refer to people with a high degree of ambulatory ability and the subsequent levels 5.0 to 9.5 refer to the loss of ambulatory ability. The range of main categories include (0)=normal neurologic exam; to (5)=ambulatory without aid or rest for 200 meters; disability severe enough to impair full daily activities; to (10)=death due to MS The clinical meaning of each possible result is the following (in which "FS" means functional system as used herein):

0.0: Normal Neurological Exam
1.0: No disability, minimal signs in 1 FS
1.5: No disability, minimal signs in more than 1 FS
2.0: Minimal disability in 1 FS
2.5: Mild disability in 1 or Minimal disability in 2 FS
3.0: Moderate disability in 1 FS or mild disability in 3-4 FS, though fully ambulatory
3.5: Fully ambulatory but with moderate disability in 1 FS and mild disability in 1 or 2 FS; or moderate disability in 2 FS; or mild disability in 5 FS
4.0: Fully ambulatory without aid, up and about 12 hrs a day despite relatively severe disability. Able to walk without aid 500 meters
4.5: Fully ambulatory without aid, up and about much of day, able to work a full day, may otherwise have some limitations of full activity or require minimal assistance. Relatively severe disability. Able to walk without aid 300 meters
5.0: Ambulatory without aid for about 200 meters. Disability impairs full daily activities
5.5: Ambulatory for 100 meters, disability precludes full daily activities
6.0: Intermittent or unilateral constant assistance (cane, crutch or brace) required to walk too meters with or without resting
6.5: Constant bilateral support (cane, crutch or braces) required to walk 20 meters without resting
7.0: Unable to walk beyond 5 meters even with aid, essentially restricted to wheelchair, wheels self, transfers alone; active in wheelchair about 12 hours a day
7.5: Unable to take more than a few steps, restricted to wheelchair, may need aid to transfer; wheels self, but may require motorized chair for full day's activities
8.0: Essentially restricted to bed, chair, or wheelchair, but may be out of bed much of day; retains self care functions, generally effective use of arms
8.5: Essentially restricted to bed much of day, some effective use of arms, retains some self care functions
9.0: Helpless bed patient, can communicate and eat
9.5: Unable to communicate effectively or eat/swallow
10.0: Death due to MS The EDSS quantifies disability in eight Functional Systems ("FS") and a neurologist or other trained professional can produce a Functional System Score ("FSS") in each of these systems by having the user complete a gold standard test. The eight Functional Systems are:
1. Pyramidal (motor function)
2. Cerebellar
3. Brainstem
4. Sensory
5. Bowel and Bladder
6. Visual
7. Cerebral or Mental
8. Other The Functional Systems (FS) are scored on a scale of 0 (low level of problems) to 5 (high level of problems) to best reflect the level of disability observed clinically. The "Other" category is not rated numerically, but measures disability related to a particular issue, like motor loss.

In the prior art, the FSS and EDSS are administered in person by a trained examiner, most often a neurologist, requiring that the patient travel to the health care facility where the examiner can administer the tests. The majority of the functional tests measure either a cognitive performance metric (such as, the Stroop Test), visual performance metric (such as the contrast sensitivity test), or an activity metric (such as the TUG test). When scoring a cognitive or visual test that has defined correct and incorrect answers, the trained examiner will also consider the time taken by the patient to supply answers to the test. Similarly when scoring an activity based test such as the TUG test, the trained examiner will consider both the time taken to perform each step in the activity and whether the activity can be completed.

A problem with the prior art is due to the standard tests being scored by observation, which does not allow for precise measurements of the time taken. A second problem is that different trained examiners can assign different scores to patients with similar performance on the tests, or equivalent scores to patients that have different performance levels on the tests. Another problem with the prior art is that because the test is administered at the trained examiner's facility, it is not possible to use the test to determine how quickly the patient's score responds to changes in medication or to diet or other events that occur with the activities of daily living.

SUMMARY OF THE INVENTION

The present invention relates to a technique in the form of an exemplary mobile application for measuring outcomes of subjects having multiple sclerosis (MS) or other neurological diseases. In the present system, the subject uses a specialized mobile application program (the "App") that evaluates cognition, afferent visual functioning, motor functioning, fine motor functioning, coordination, gait, and endurance by evaluating data representing both the time taken and the accuracy of the subject's ability to perform a program of activities that are presented by the mobile App using specially designed tests and information obtained from certain sensors on the mobile device. The subject establishes a mobile app session by logging into the App with a unique identifier. This identifier is used to establish a connection with a computer service that authenticates the user, and then stores a permanent representation of the data that is collected during the user's session with the mobile application in a computer cloud environment. Once the data has been stored in the cloud, a computer service is used to analyze the data. The computer service uses up to three machine learning algorithms that establish the correlation of the application data to the gold standard activities that are currently used by clinicians.

The foregoing deficiency and problems in the prior art has been solved in accordance with the present invention which relates to a specialized mobile App with a defined set of cognitive, visual function, and activity tasks that execute on a mobile device that correspond to the functional tests that are described in the prior art. The mobile App uses information obtained from certain mobile device sensors to detect activity state transitions.

The user first establishes a mobile app session by logging into the App with a unique identifier. This identifier is used to authenticate the user and to establish a connection with a computer service that stores a permanent representation of the data that is collected during the App session.

After the user establishes a session on the mobile App, in the preferred embodiment the App presents a page labeled "Wellness Workout" that presents a list of available activities that the user can launch. By selecting the icon corresponding to a particular activity, the App will execute a particular software implementation of the specialized test.

Each time the mobile App determines that one of these events has occurred, the App records a new state transition, and saves information on the mobile device describing the event including the event type recorded, the event type the App was expecting, the time taken from the previous event to the current event in milliseconds (ms). The mobile App determines activity state changes by reading the data values of particular device sensors and looking for certain changes in the data values that correspond to the user stopping or starting various motions.

The App user may complete only certain activities during a particular session. For each of these activities, the mobile App saves data corresponding to each state transition using storage provided by the mobile device until the mobile device can connect to the computer service by either a wireless connection, or by a wired connection to a computer with an internet connection. When the connection becomes available the mobile App transfers an encrypted representation of the data corresponding to each activity that the user performed during the session to the computer service. The computer service stores a permanent representation of the data in a distributed computer environment known as a cloud. After the data is stored in a cloud, the data produced from each activity is then analyzed by 3 machine learning algorithms that will produce a classification of the data. By using a specially designed web interface, a physician or other healthcare specialist can review the activities and classifications of those patients under their care, over different time intervals to determine if the users performance has changed over time, reflecting a change in severity of the disease.

The mobile App implementation solves the deficiencies of the prior art by increasing the timing accuracy of the data produced while the user is performing the tests, and by eliminating the requirement that user be observed by a trained examiner while performing the tests.

There are eleven activities that are implemented in the mobile App, that correspond to particular Gold standard tests that trained examiners use to assign Functional System Scores to patients. These activities are accessible from the Wellness Workout Page after successfully logging into the mobile App. The activities can be grouped according to the type of skill the test is measuring. A test involving walking or a repetitive arm movement is implemented by the App as a sequence of directed state transitions, where each transition is determined by a change in data from several more mobile device sensors, ie the accelerometer, gyroscope or magnetic sensor.

BRIEF DESCRIPTION OF THE DRAWINGS

The invention will become more readily apparent from the following description of preferred embodiments thereof as shown by way of example only in the accompanying drawings.

The invention will become more readily apparent form the following description of preferred embodiments thereof shown by way of example only in the accompanying drawings.

DETAILED DESCRIPTION OF THE INVENTION

Figure 1A:
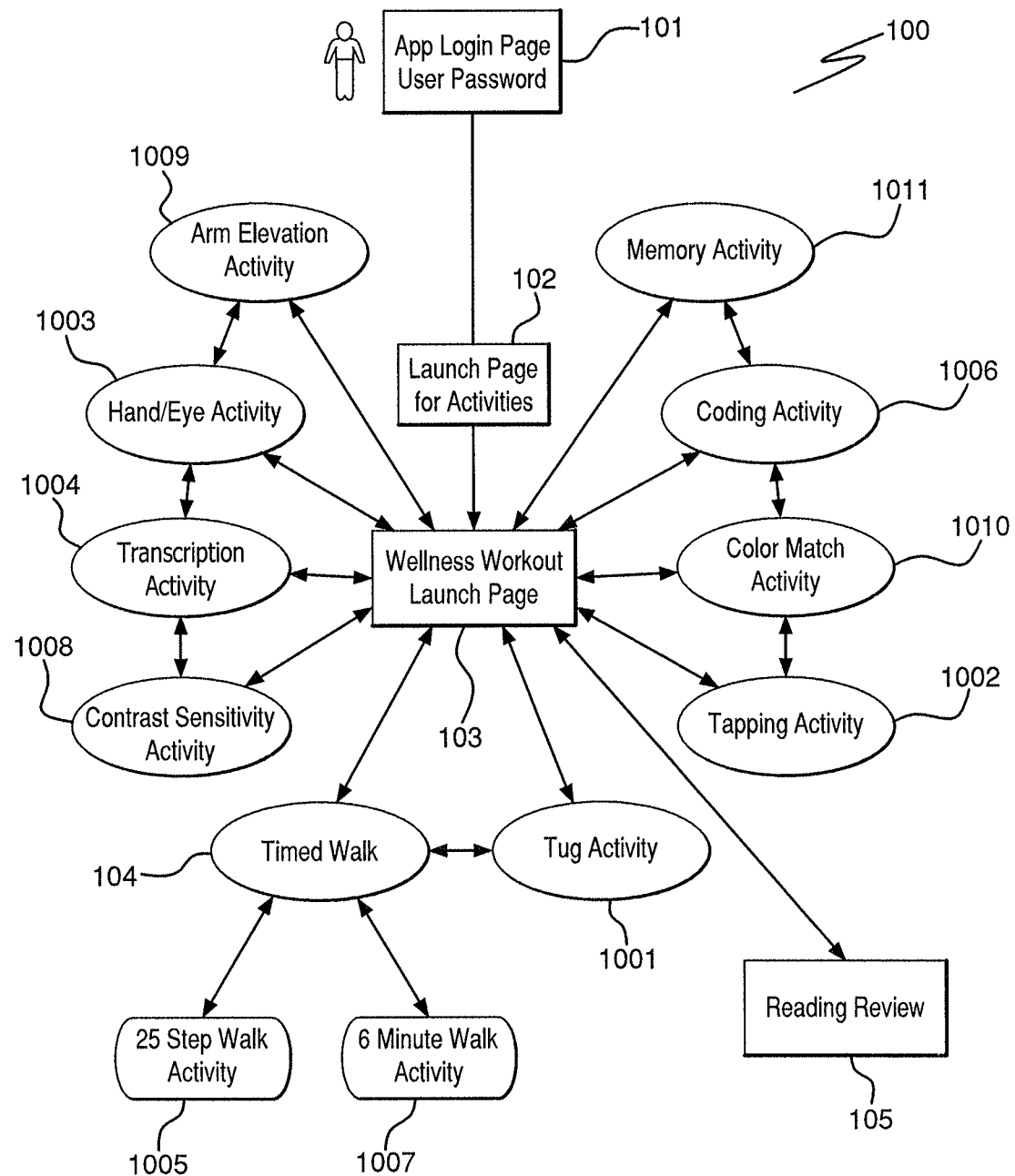
FIG. 1A is a block diagram for the mobile application program that describes a segment of the method of the present invention.

The present invention relates to a technique in the form of an exemplary mobile application for measuring outcomes of subjects having MS or other neurological diseases. In the present system, the subject uses a specialized App as shown by a block diagram therefor 100 in FIG. 1A that evaluates cognition, afferent visual functioning, motor functioning, fine motor functioning, coordination, gait, and endurance by evaluating data representing both the time taken and the accuracy of the subject's ability to perform a program of activities that are presented by the mobile App using specially designed tests and information obtained from certain sensors on the mobile device. The subject establishes a mobile App session in mobile device 200 in FIG. 1B by logging into the App with a unique identifier at block 101 of FIG. 1A. Mobile device 200 is selected from a range of commercially available hand held smartphones, such as the Apple iPhone or Samsung Galaxy. This identifier is used to establish a connection on a secured link 400 with a computer service in cloud 300 of FIG. 1B that authenticates the user, and then stores a permanent representation of the data that is collected during the user's session with the mobile application in a computer cloud environment 300. Once the data has been stored in the cloud 300, a computer service (not shown) is used to analyze the data. The computer service uses up to three machine learning algorithms that establish the correlation of the application data to the gold standard activities that are currently used by clinicians.

The specialized mobile App has a defined set of cognitive, visual function, and activity tasks that execute on mobile device 200 that correspond to the functional tests that are described in the prior art. The mobile App uses information obtained from certain mobile device 300 sensors to detect activity state transitions as further described herein.

After the user establishes a session on the mobile App, in the preferred embodiment the App is launched at block 102 and then presents on the screen of the mobile device 200 the opening screen 1030 labeled "Wellness Workout" that presents a list of available activities that the user can launch. By selecting an icon from the group of icons on screen 1030, such as icon 1031 (Arm Elevation); 1032 (Snooker); 1033 (Transcription Test); 1034 (Contrast Sensitivity); 1035 (Timed Walk); or 1036 (Tug Test): corresponding to a particular activity as shown in blocks 1001 through 1011 in FIG. 1A, the App will execute a particular software implementation of the specialized test.

Figure 1B:
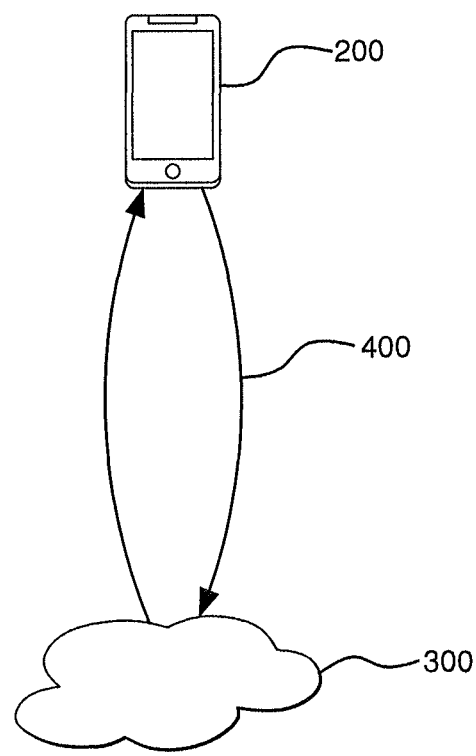
FIG. 1B is a flowchart describing the system of the present invention.
Figure 2:
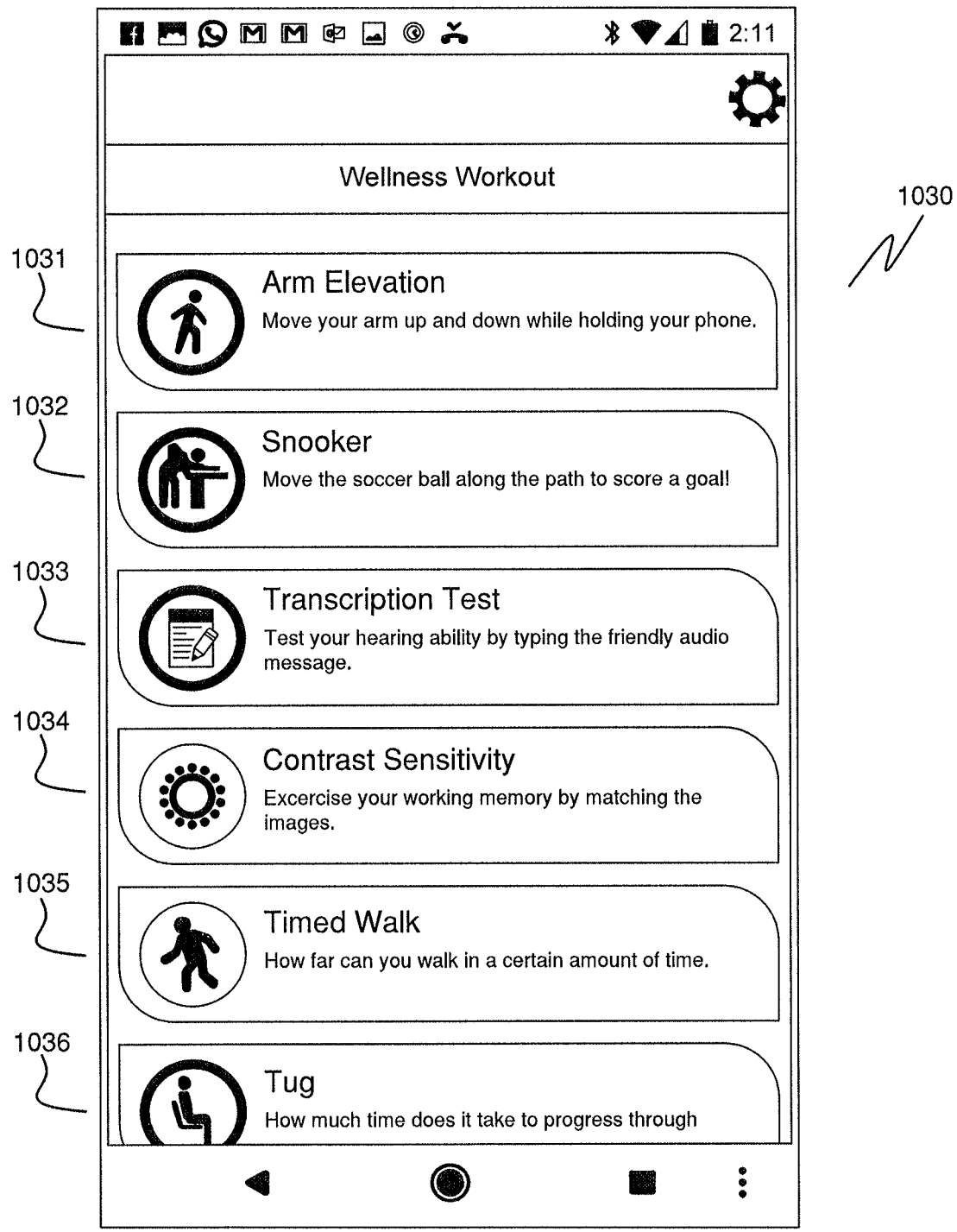
FIG. 2 is a screenshot of the launch screen of the application of the present invention.

Each particular mobile App implementation has a unique sequence of steps the user must complete that correspond to a standard functional test, for example, if the User chooses "Transcription Test" icon 1033 from the Wellness Workout page 1030 at block 1004 of FIG. 1A, the App executes a mobile software implementation corresponding to the Auditory Comprehension typing Test (ACT). A standard motor skill activity can involve walking at block 1104 which corresponds to icon 1035 (25 step walk at block 5 and 6 minute walk at block 7), repetitive arm movement at block 9 which corresponds to icon 1031, or the TUG test at block 1001, which corresponds to icon 1036, involves the user transitioning from sitting to standing to walking to turning and then returning to the starting point. The App implementation of these activity tests use the mobile device 200 accelerometer, gyroscope or magnetic sensor to determine when the user has taken a step, transitioned his position or orientation or moved his arms. Each of the eleven tests of the preferred embodiment are described in greater detail herein.

Each time the mobile App determines that one of these events has occurred, the App records a new state transition, and saves information on the mobile device describing the event including the event type recorded, the event type the App was expecting, the time taken from the previous event to the current event in milliseconds (ms). The mobile App determines activity state changes by reading the data values of particular device 200 sensors and looking for certain changes in the data values that correspond to the user stopping or starting various motions.

The App user may complete only certain activities during a particular session. For each of these activities, the mobile App saves data corresponding to each state transition using storage provided by the mobile device until the mobile device can connect to the computer service by either a wireless connection, or by a wired connection to a computer with an internet connection. When the connection becomes available the mobile App transfers an encrypted representation of the data corresponding to each activity that the user performed during the session to the computer service. The computer service stores a permanent representation of the data in a distributed computer environment known as a cloud 300. After the data is stored in cloud 300, the data produced from each activity is then analyzed by one of three machine learning algorithms that will produce a classification of the data.

By using a specially designed web interface at block 105, a physician or other healthcare specialist can review the activities and classifications of those patients under their care, over different time intervals to determine if the users performance has changed over time, reflecting a change in severity of the disease.

The mobile App implementation solves the deficiencies of the prior art by increasing the timing accuracy of the data produced while the user is performing the tests, and by eliminating the requirement that user be observed by a trained examiner while performing the tests.

There are eleven activities as shown in blocks 1 through 11 on FIG. 1A that are implemented in the mobile App, that correspond to particular Gold standard tests that trained examiners use to assign Functional System Scores to patients. These activities are accessible from the Wellness Workout page 1030 after successfully logging into the mobile App. The activities can be grouped according to the type of skill the test is measuring. A test involving walking or a repetitive arm movement is implemented by the App as a sequence of directed state transitions, where each transition is determined by a change in data from several more mobile device 200 sensors, such as an accelerometer, a gyroscope, or a magnetic sensor.

In the preferred embodiments, the eleven activities are described in greater detail as set out below:

Activity 1: The Timed Up and go (TUG) Test

Figure 3A:
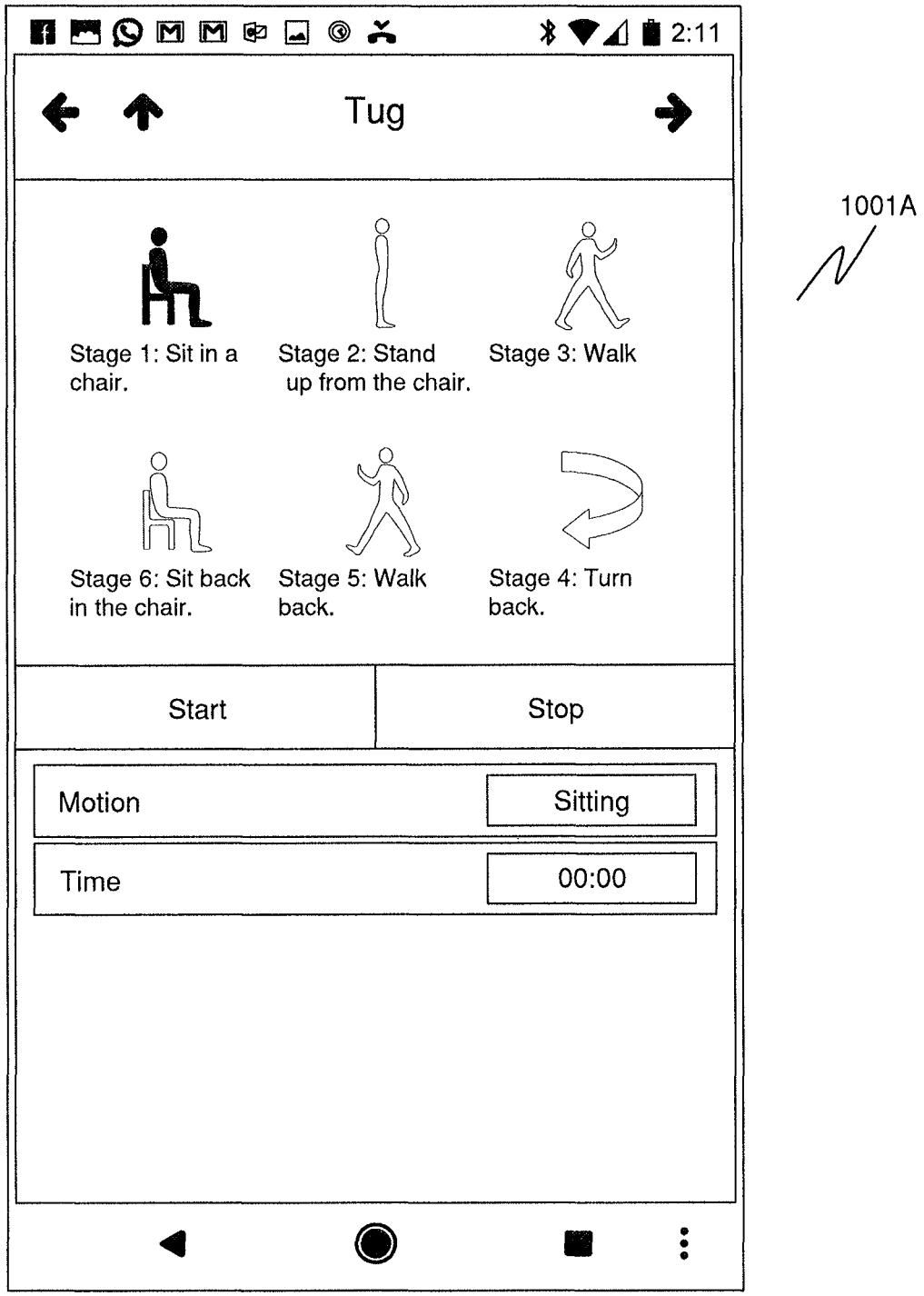
FIGS. 3A, 3B, 3C, 3D, 3E, and 3F together are the progression of screen shots making up the Timed Up and Go Test of the present invention.
Figure 3B:
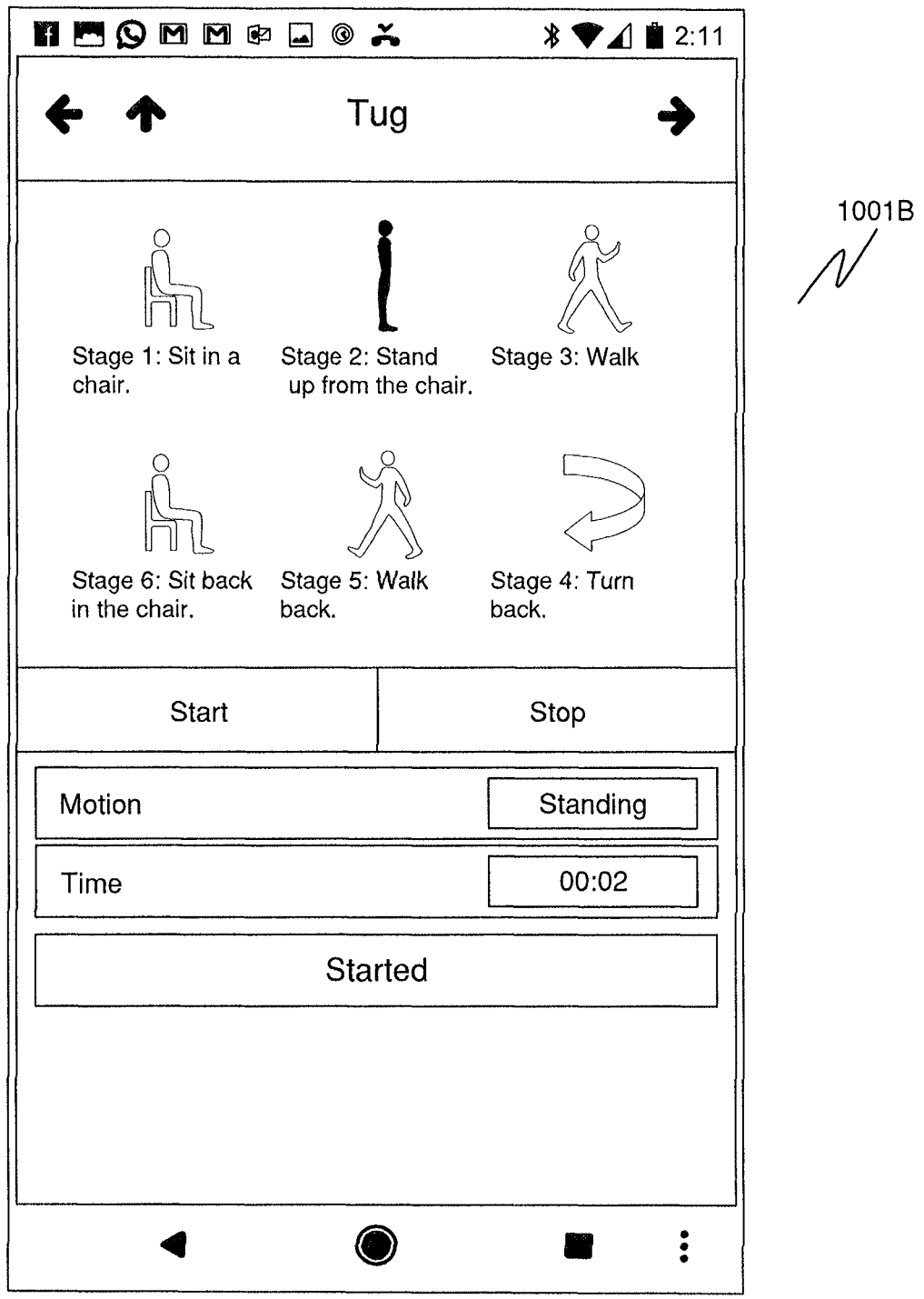

In FIG. 1A this activity is part of the block diagram 100 at block 1001. The mobile App displays an instruction page at screen shot 1001A on FIG. 3A that instructs the user to hold their mobile device steady in their hand and to proceed through a sequence of states starting with the state [sitting], and proceeding to the state[standing up] as directed by screen shot 1001B in FIG. 3B.

Figure 3C:
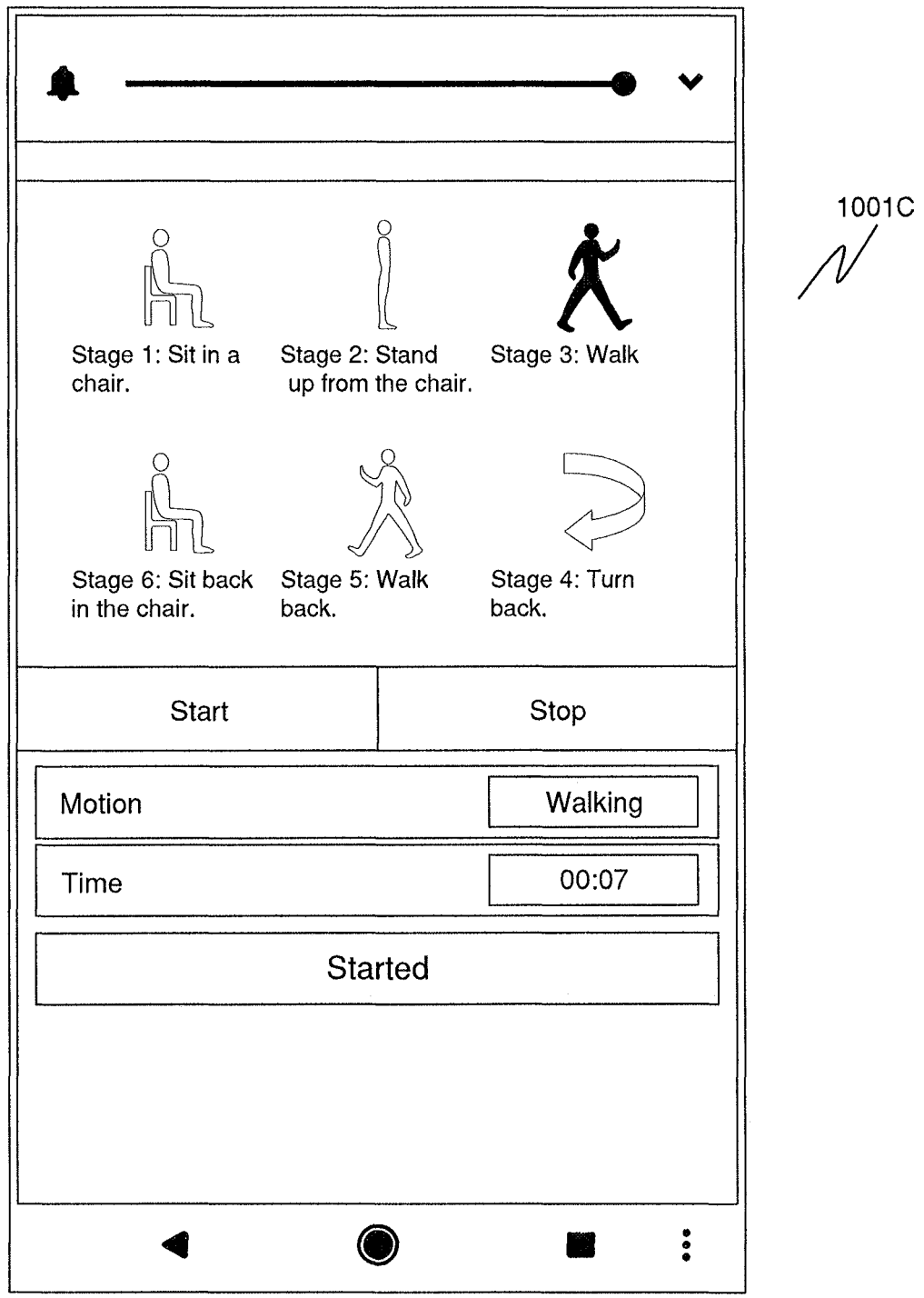
Figure 3D:
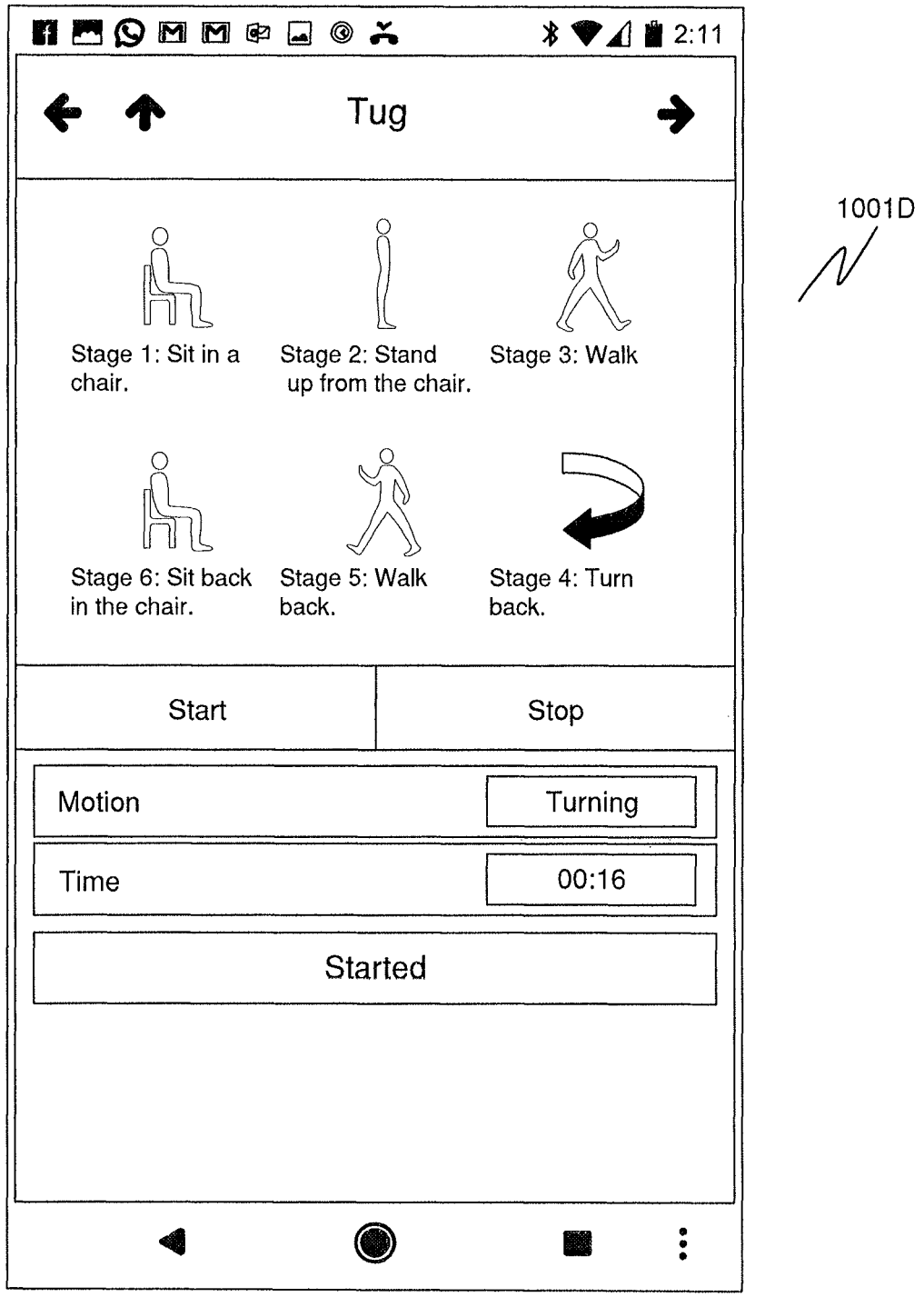
Figure 3E:
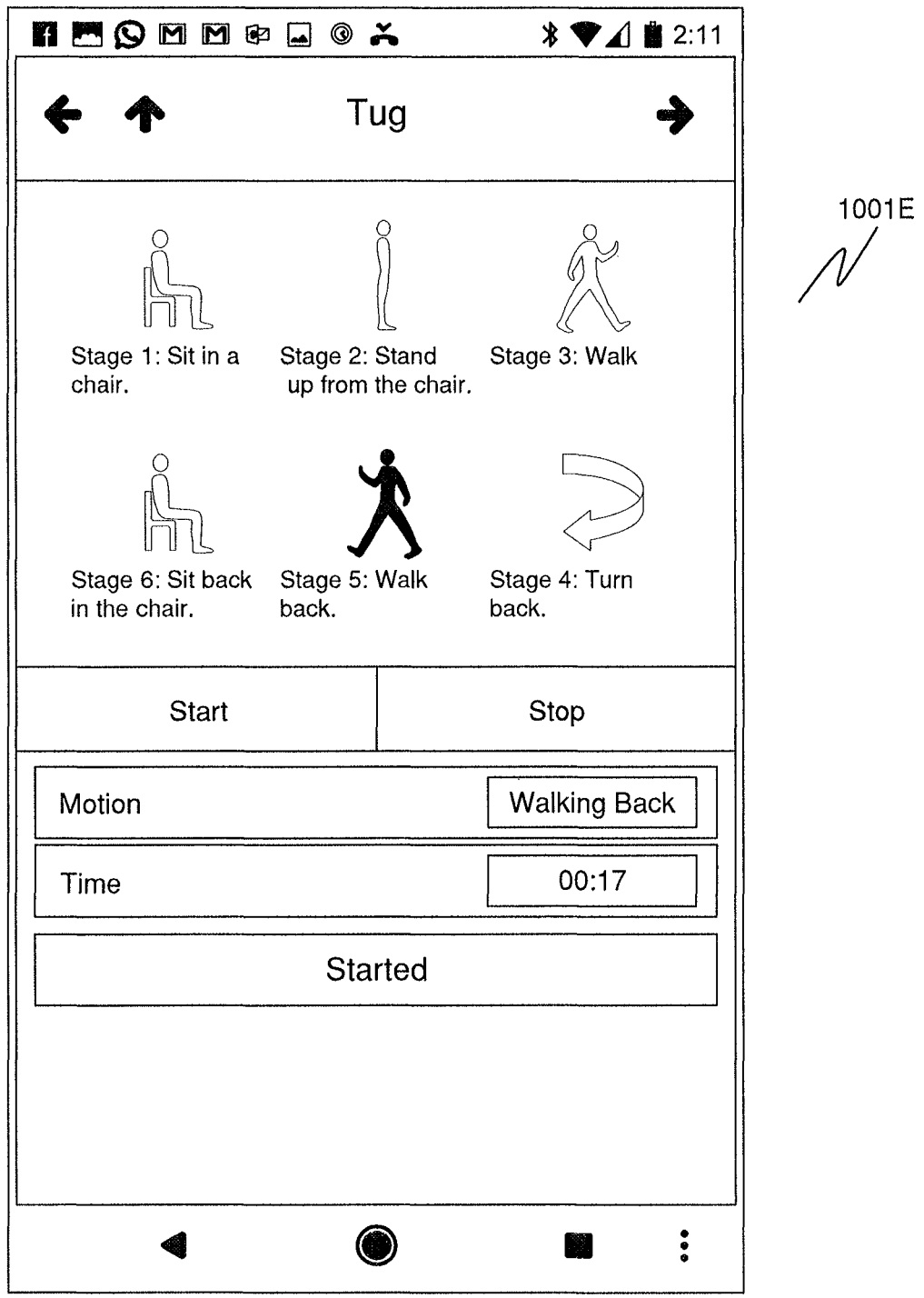
Figure 3F:
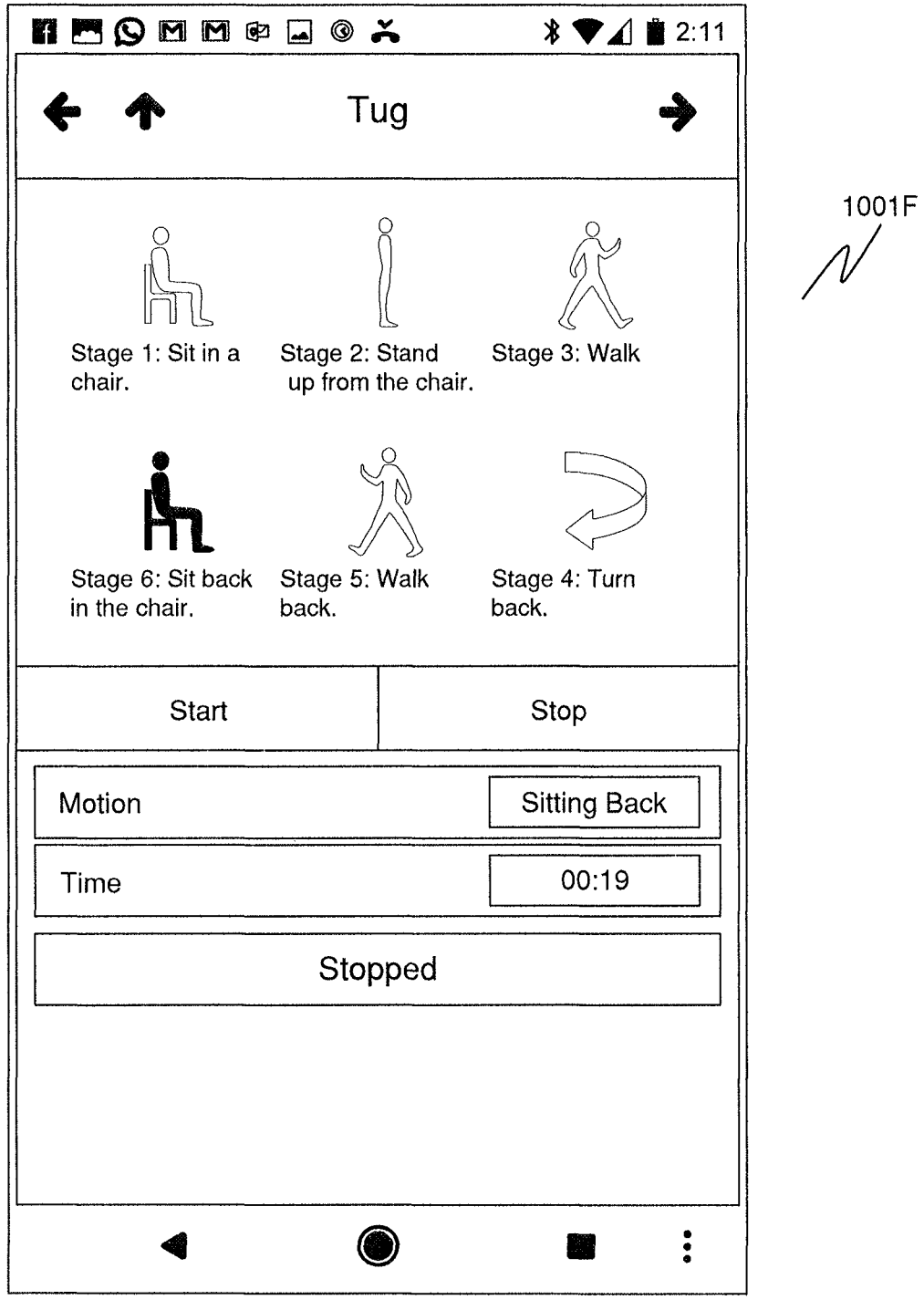

The user is directed by screen shot 1001C on FIG. 3C to the next state is to [walk at least 2 steps], followed by the direction of screen shot 1001D state [turn around 180 degrees], followed by the direction in screen shot 1001E as shown in FIG. 3E for the state [walk back to the chair] and the final state [sit to finish] as shown by screen shot 1001F in FIG. 3F.

The App presents a series of icons paired with a short description that indicate the states that the user will transition through. Initially the "sitting icon" is highlighted by the mobile App after the user touches the "Start" icon. The mobile App continually reads changes in data from the accelerometer, gyroscope and magnetic sensor to determine that the user has transitioned from one state to the next state. The current state is highlighted so that the user can see that the mobile App has detected their transition from one state to the next. Each time the mobile App detects that a transition has occurred, it highlights the current icon in the sequence and records an event type which represents the current state the user is in, the expected position the user should be in, and the time from the previous event to the current event in milliseconds (ms). The complete set of state transitions is displayed in Appendix A.

When the user initiates this TUG activity at block 1001, the App displays an instruction page displaying that the activity has 6 stages and that the user should hold the mobile device steady while performing the activity. The 6 stages are:

1. User is sitting
2. User is standing
3. User is walking
4. User is turning around
5. User is walking back
6. User is sitting to finish The App associates each stage with a particular software representation (state). The app records a state transition each time the user leaves the current stage for the next stage.

The App detects a state transition by observing certain changes in the values that are continually generated by reading data generated by the particular motion sensors that are included as hardware components of the mobile device. The particular motion sensor values used by the App are from the accelerometer, gyroscope and magnetic sensor.

Although the values obtained from the motion sensors are constantly changing, the changes between successive values can be used to determine whether the mobile device is in motion or is stationary. When the device 200 is in motion, the changes between successive values of the accelerometer become larger and when the motion slows down, the changes between successive values become smaller. This is true for the other motion sensors as well and by using data obtained from several sensors it is possible to increase the accuracy that the App can determine when a motion has started and when it has ended. The mobile App determines that a state transition is starting by reading increasing changes in the successive sensor changes, and that the state transitioned has concluded by reading small magnitude changes in the successive sensor changes. Each time a state transition has concluded the mobile App creates an Event with a particular software representation. This representation encodes the stage, sequence number, the time from the previous event in milliseconds and other information that identifies the current stage of the activity.

Activity 2: Fine Motor Function/Rapid Finger Movement Test

In FIG. 1A this activity is part of the block diagram 100 at block 1002. The mobile App displays an instruction page at screen shot 1002A on FIG. 4A an image of a treasure chest in the center of the mobile device screen and two icons indicating start 1002A1 and stop 1002A2. After the user touches the start icon, there is a short countdown after which the mobile App displays an image of a coin 1002A3 on a designated position on the mobile device screen. The user is instructed to tap the coin image 1002A3 as frequently as possible for 10 seconds.

Figure 4A:
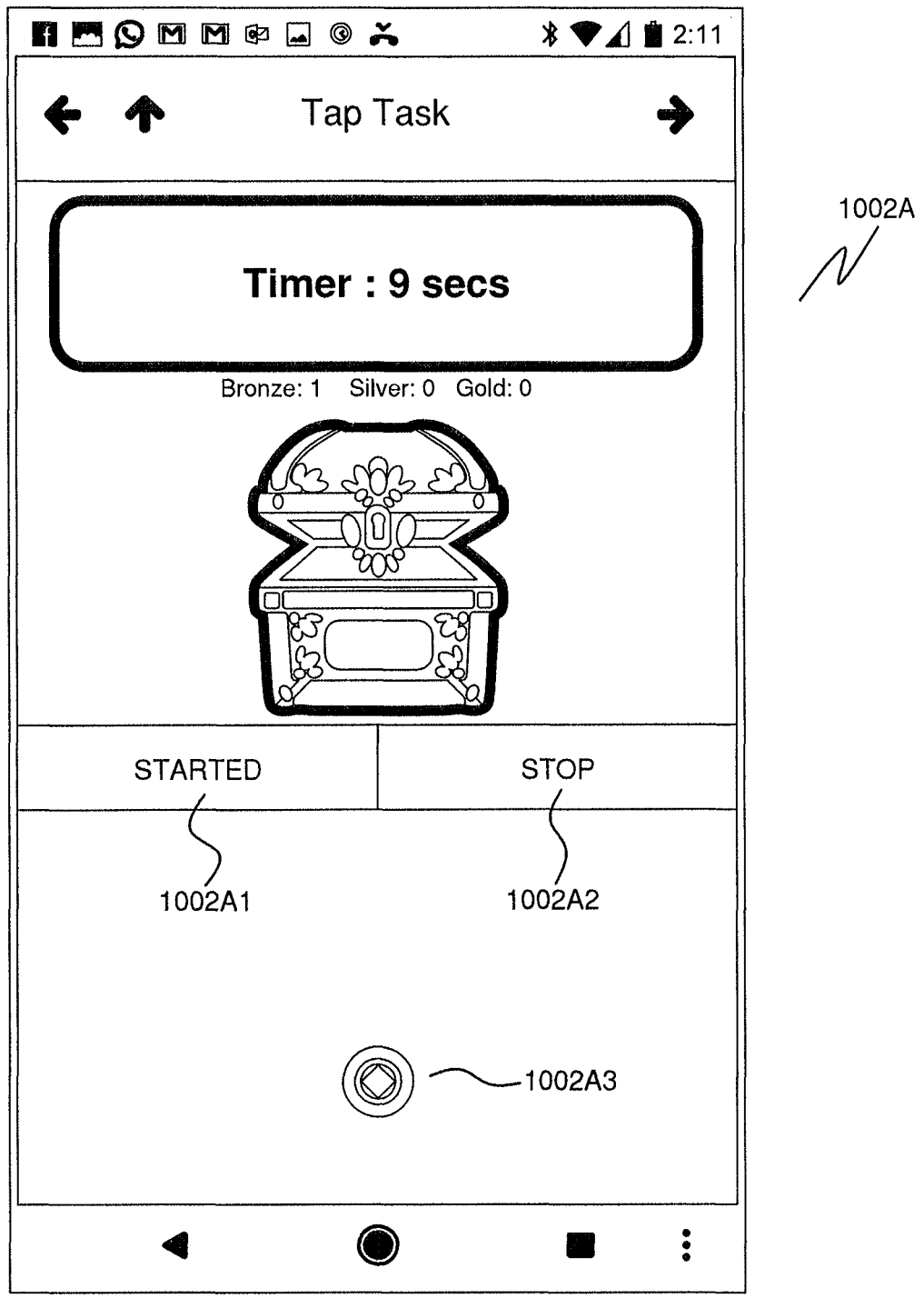
FIGS. 4A, 4B, and 4C illustrate the user's view of the screen of the application in connection with the Fine Motor Function/Rapid Finger Movement of the present invention.
Figure 4B:
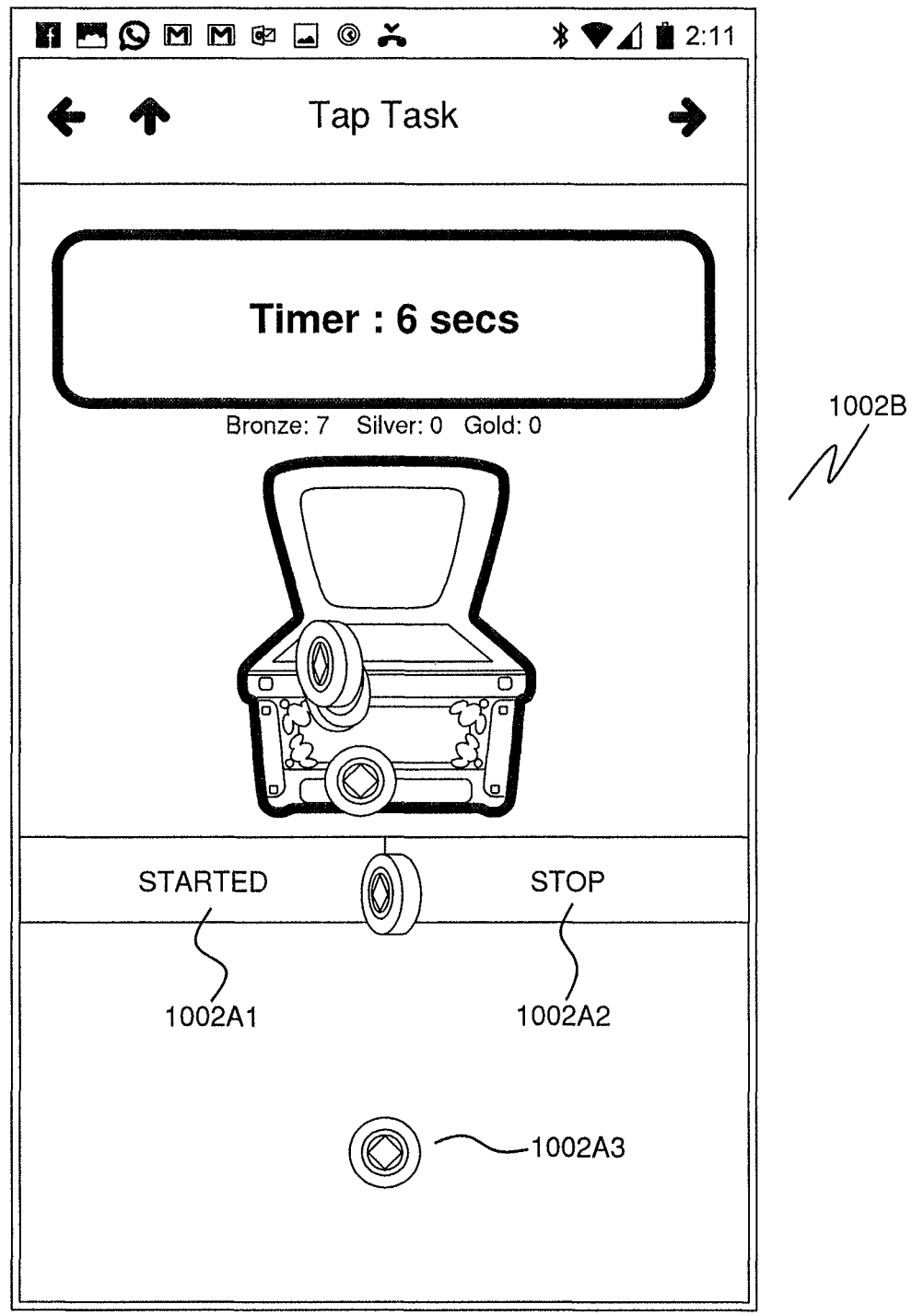
Figure 4C:
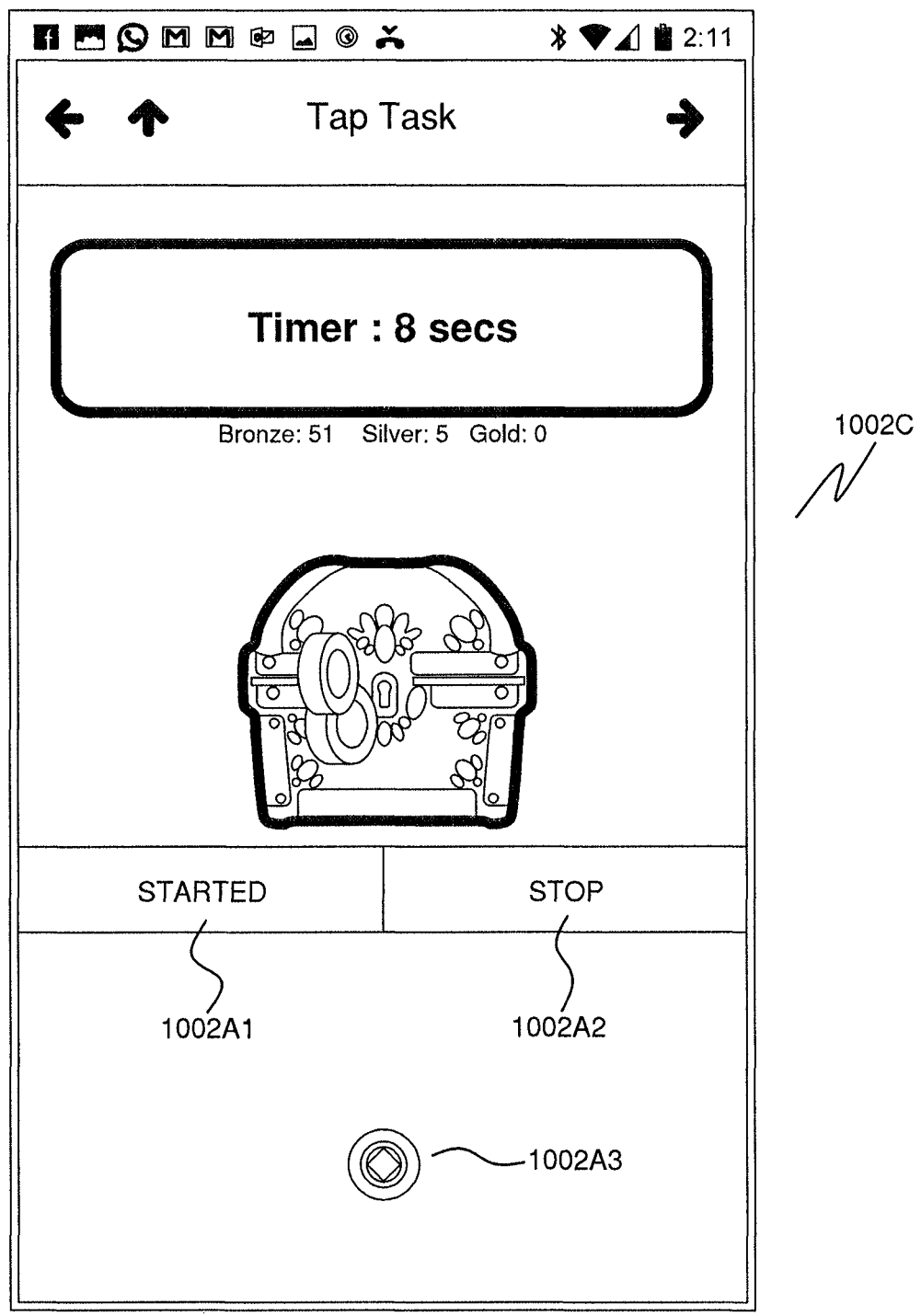

The test will be repeated three times first using a bronze coin as shown in the screen display 1002A in FIG. 4A, next with a silver coin as shown in screen display 1002B in FIG. 4B, and finally with a gold coin as shown on screen display 1002C in FIG. 4C. Each time the coin image 1002A3 is tapped, the mobile app records an event representing the screen position that was tapped, the designated screen position and the time from the previous event to the current event in milliseconds (ms).

Activity 3: Upper Extremity Coordination Test

Figure 5A:
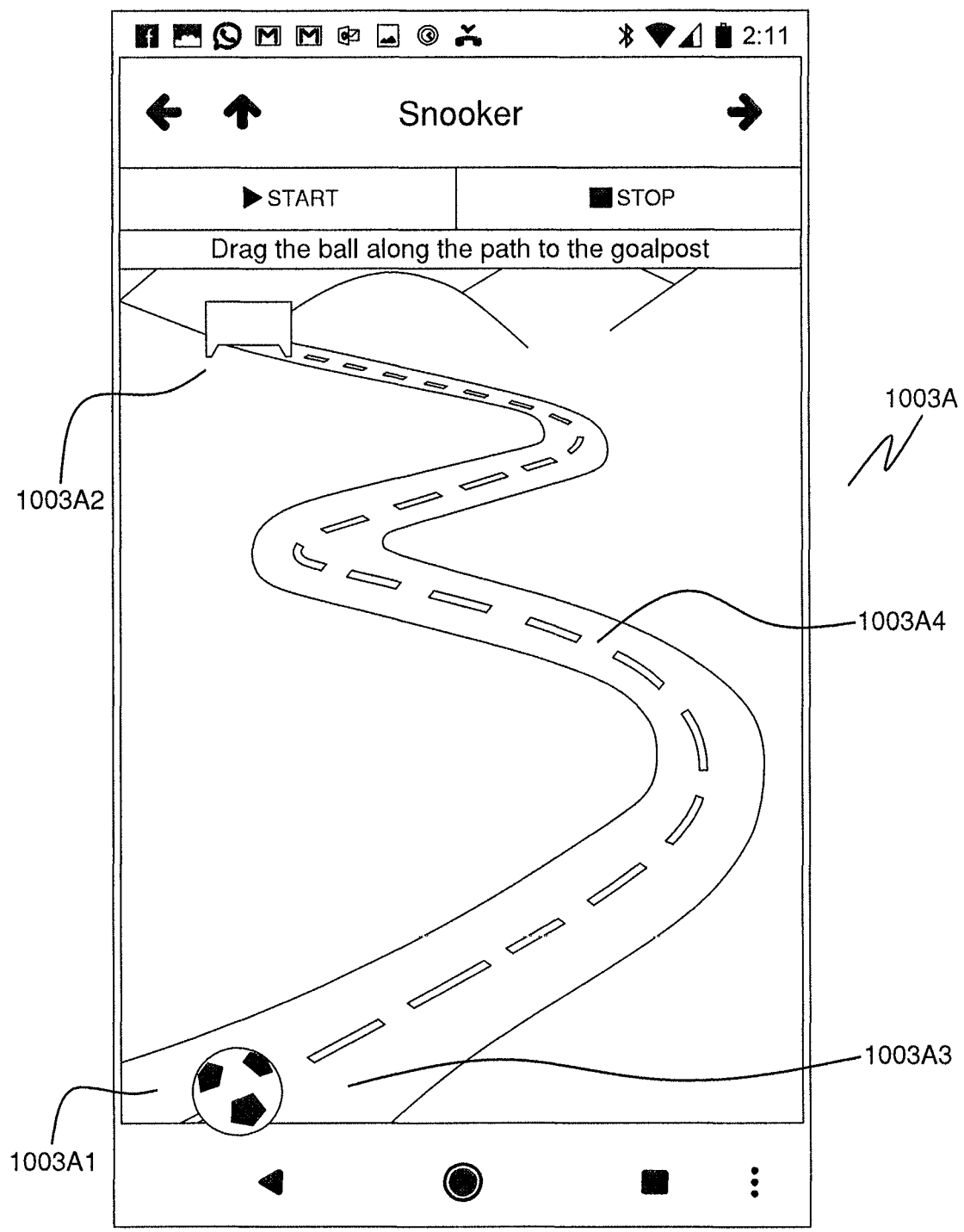
FIGS. 5A, 5B, 5C, and 5D illustrate the user's view of the screen of the application in connection with the Upper Extremity Coordination test of the present invention.

In FIG. 1A this activity is part of the block diagram 100 at block 1003. The mobile App displays an instruction page at screen shot 1003A on FIG. 5A an image of a path with a starting point 1003A1 and a goalpost 1003A2, and the user is asked to drag the image of an object, in the preferred embodiment a soccer ball 1003A3, with their index finger such that it stays within the boundaries of the path 1003A4. The test will be repeated three times on each hand. The mobile App represents points on the mobile device display as a set of (x, y) values such that the x values correspond to the number of pixels from the left end of the screen, and the y values correspond to the number of pixels from the bottom of the screen. x will vary from 0 to a device dependent value Xmax, and y will vary from 0 to a device dependent value Ymax. The path 1003A4 is considered to be a sequence of points (xp, yp) that correspond to the image of the path on the screen.

Figure 5B:
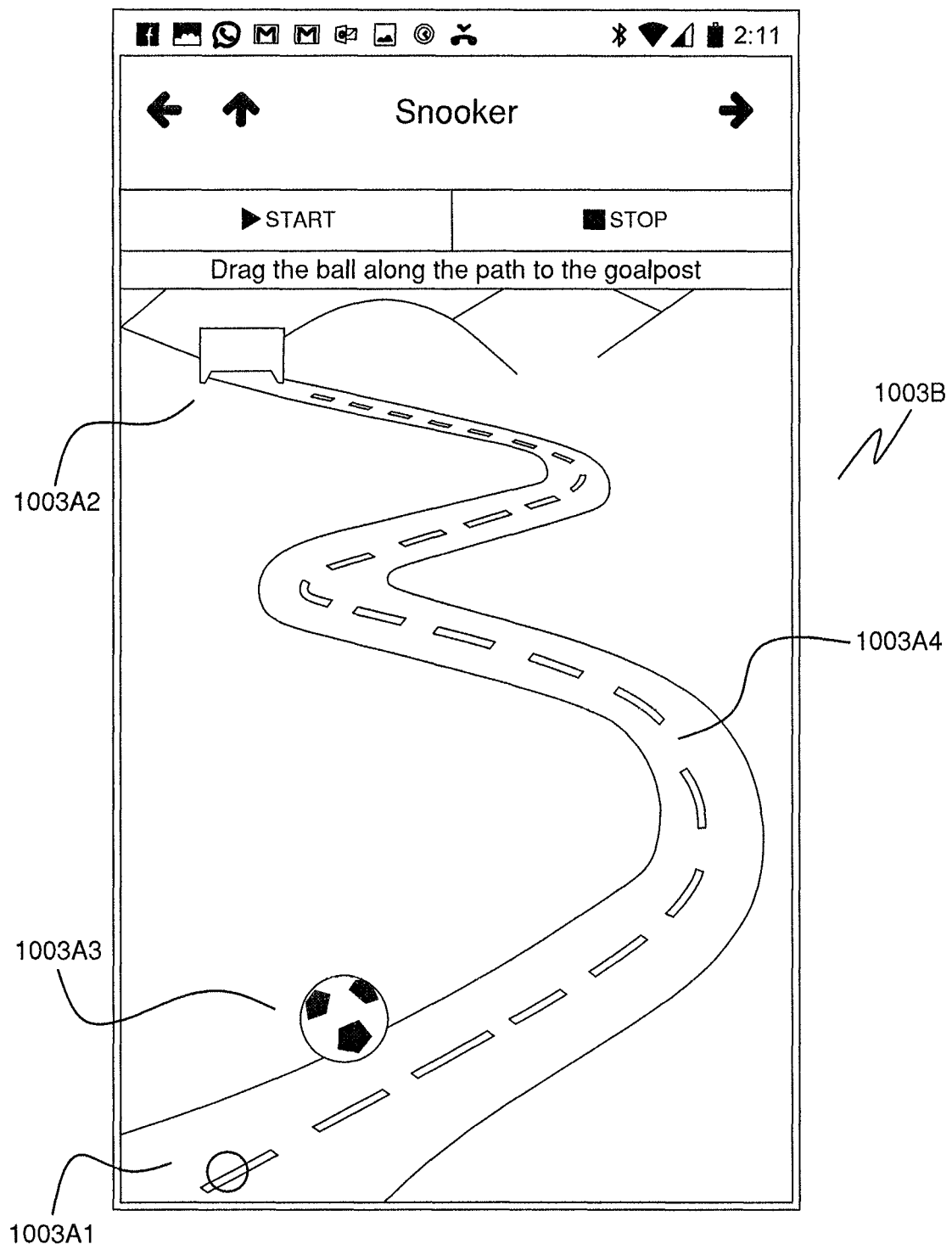
Figure 5C:
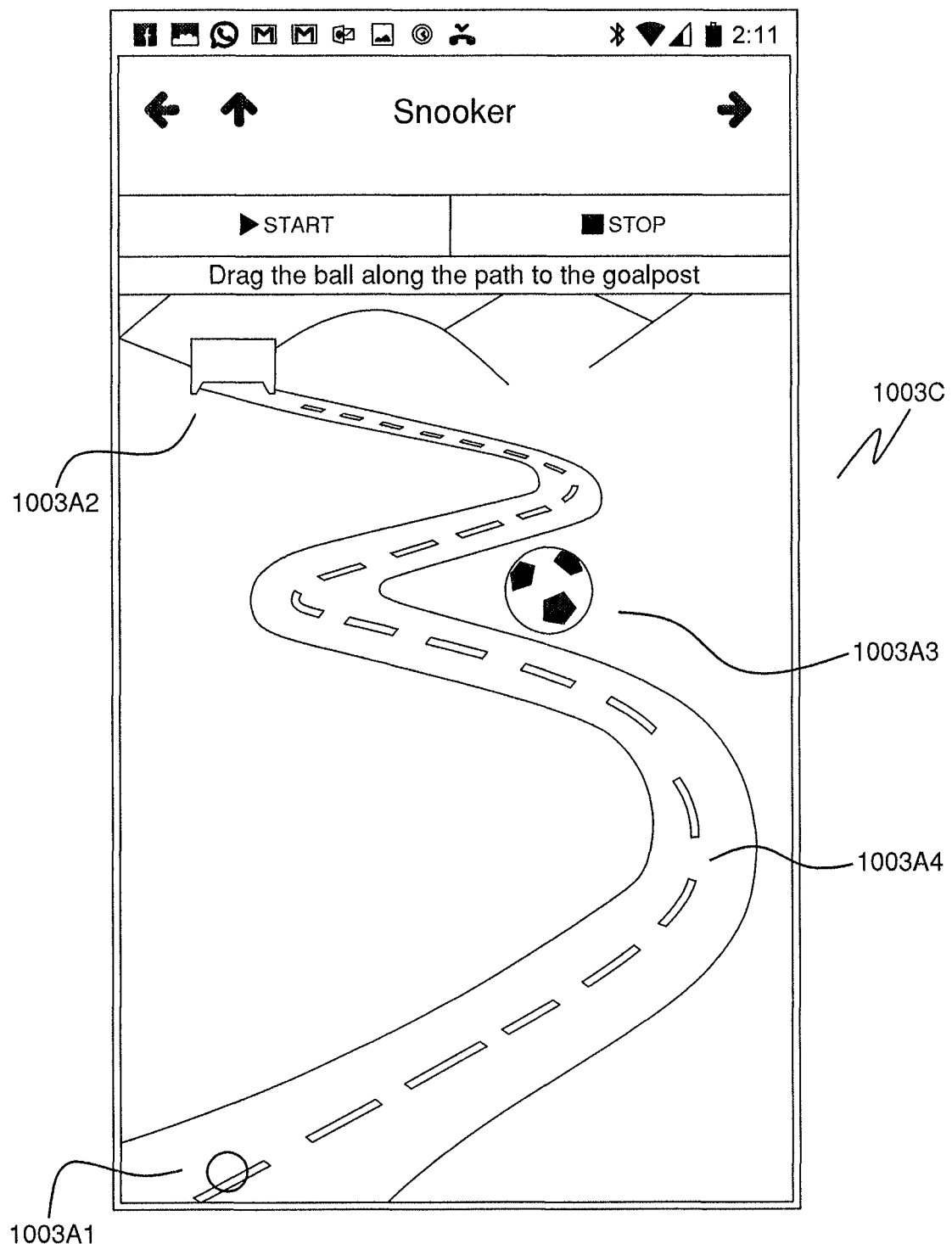
Figure 5D:
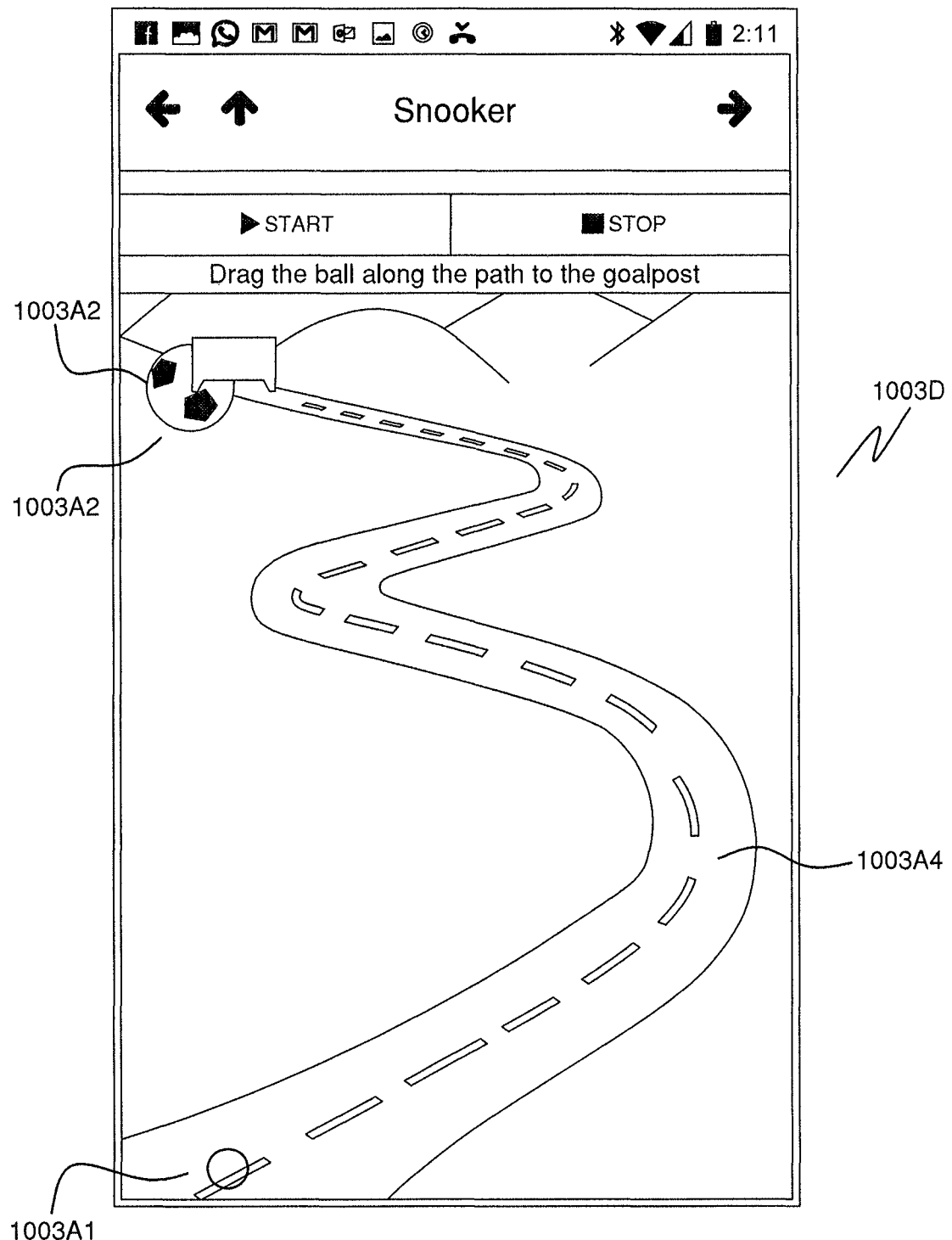

Progress on the path is represented by increasing values of yp. ie if the user dragged the object 1003A3 to a point (x1, y1) as shown in screen display 1003B on FIG. 5B and then drags the object to (x2, y2) as shown in screen display 1003C on FIG. 5C. The object is progressing on the path 1003A4 if y2>y1).

If the user dragged the object icon to a screen location (x1, y1) and (xp, y1) is the corresponding screen location of the path 1003A4, then the deviation from the path 1003A4 at y1 is the value (x1−xp). When the user presses the screen at a point with a y value that is at least 3 units away from the previous selected y value, the mobile app records this position as a new state transition and saves an event to the mobile device storage. This event represents the last screen position as shown in screen display 1003D in FIG. 5 that was tapped, the corresponding path position and the time from the previous ent to the current event in milliseconds (ms).

Activity 4: Auditory-Comprehension-Typing Test (ACT) Test

In FIG. 1A this activity is part of the block diagram 100 at block 1004. The mobile App displays an instruction page at screen shot 1004A on FIG. 6A that encompasses a quadrant keyboard 1004A1 on the mobile device screen (a virtual keyboard where the letters are in alphabetical order but are distributed among 4 quadrants) and uses the mobile device speaker to play a sound file (WAV file) corresponding to a short random phrase such as "No Problem" as shown on FIG. 6A along with a sequence of boxes 1004A2 corresponding to each letter in the phrase. The user must select letters from the quadrant keyboard that spell out the phrase. Each time a letter is selected, the application inserts the letter into the leftmost available box and indicates to the user whether the letter was correct or incorrect along with the total amount of time taken from the first letter that was selected to the current letter as shown in screen display 1004A in FIG. 6A. The application keeps track of the sequence of letters that the user selected from the quadrant keyboard, the correct letter in the sequence, and the duration in milliseconds (ms) from the previous time a letter was selected until the current time the user selected a letter by saving a representation of the data on the mobile device.

Figure 6A:
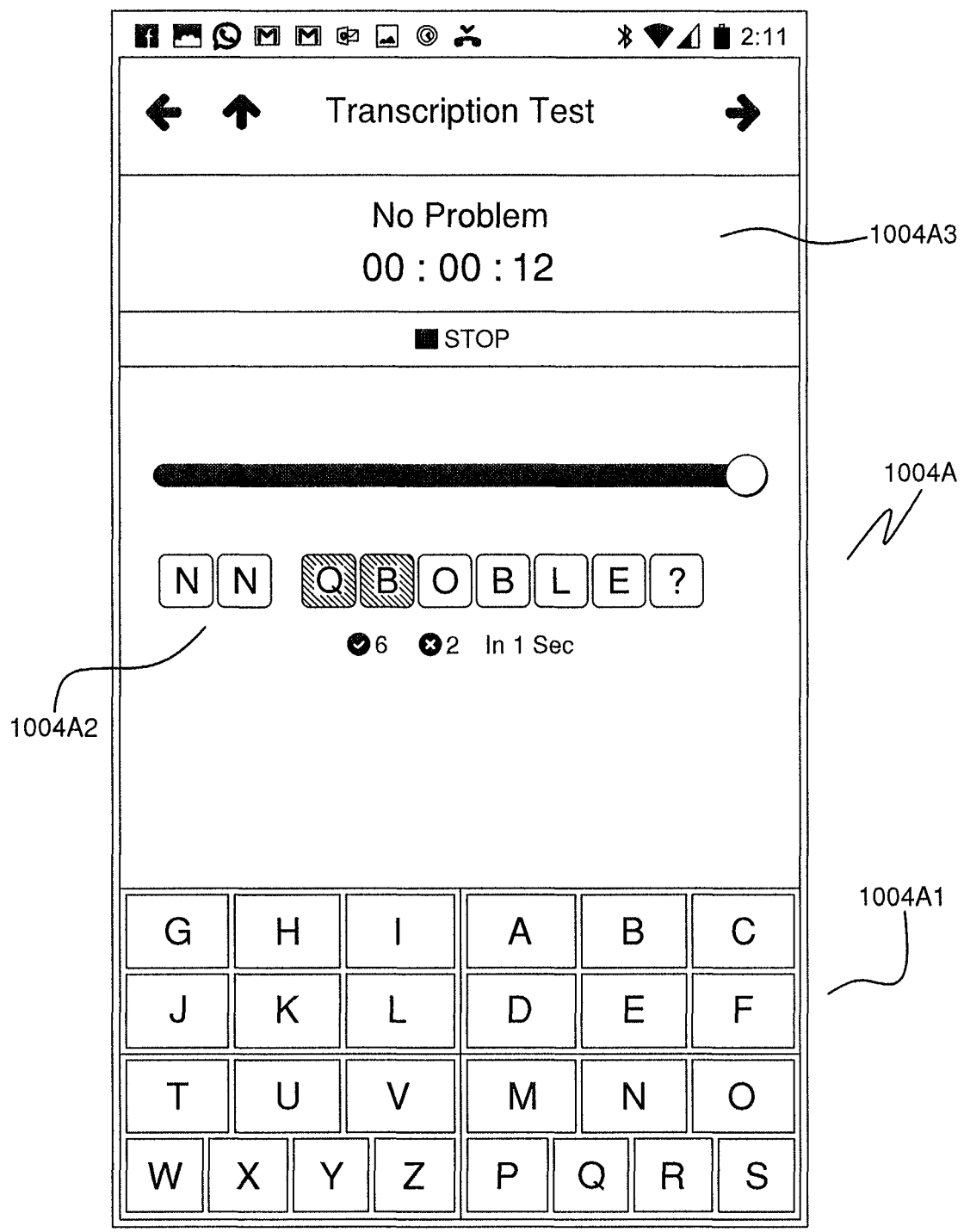
FIGS. 6A, 6B, 6C, and 6D illustrate the user's view of the screen of the application in connection with the Auditory Comprehension Typing test of the present invention
Figure 6B:
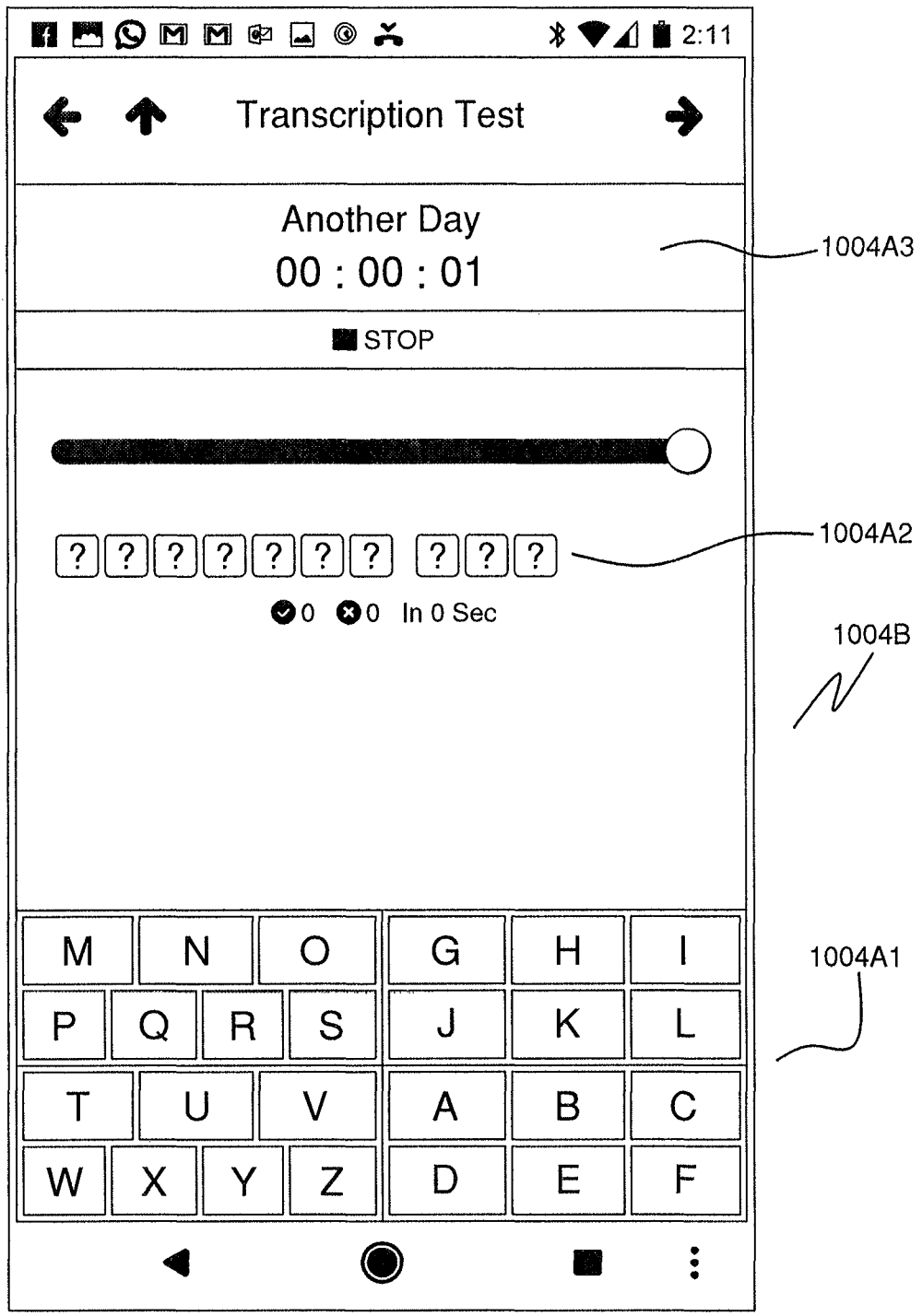
Figure 6C:
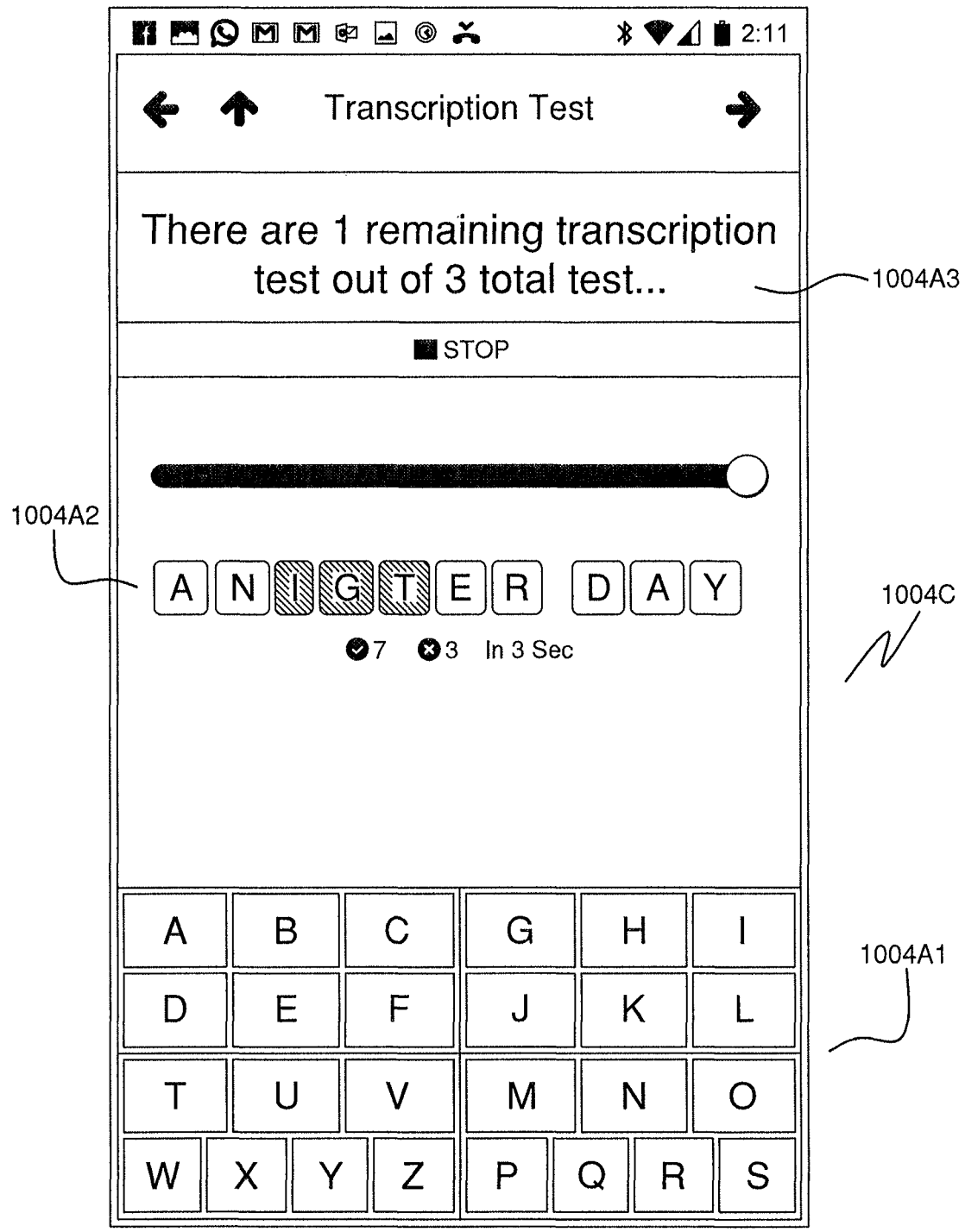
Figure 6D:
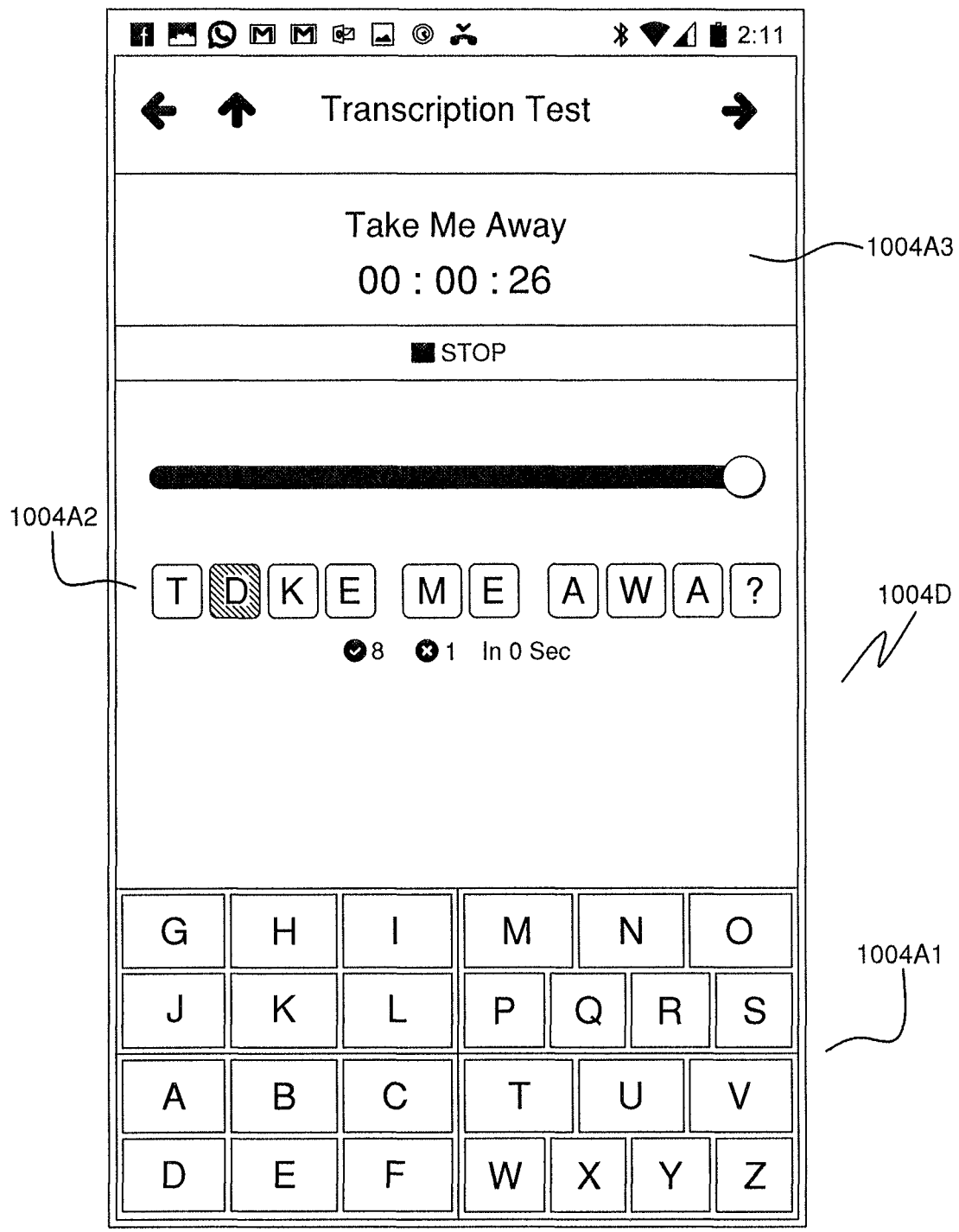

This implementation uses the mobile device speaker to play three sound file (WAV file) corresponding to a short random phrase such starting with "No Problem" in FIG. 6A and sequencing to "Another Day" as in screen display 1004B of FIG. 6B. Screen display 1004C shows the result of the user input to "Another Day" and indicates at message display 1004A3 that the third test awaits the user and that test is based on the phrase "Take Me Away" that is played when screen display 1004D on FIG. 6D is next shown to the user. Each time a letter is selected, the mobile App inserts the letter into the leftmost empty box and indicates to the user whether the chosen letter was correct or incorrect, along with the total amount of time taken from the time the first letter that was selected, to the current letter. Each time a letter is selected the mobile App records a new state transition. The application keeps track of the sequence of letters that the user selected from the quadrant keyboard, the correct letter in the sequence, and the duration in milliseconds (ms) from the previous time a letter was selected until the current time the user selected a letter by saving a representation of the state transitions on the mobile device.

Activity 5: Timed 25-Step Walk

Figure 7:
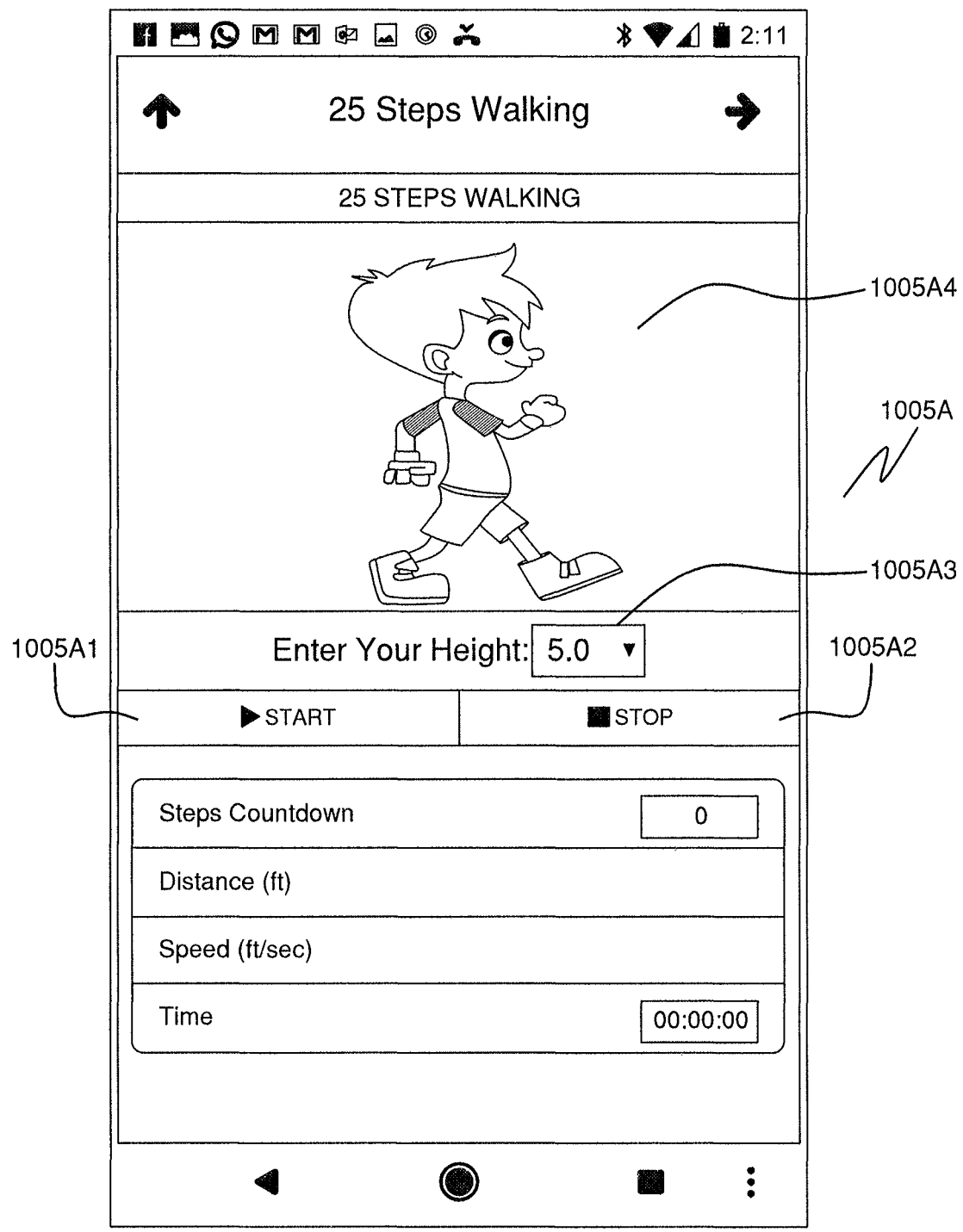
FIG. 7 is a representative screen shot from the Timed 25 Step Walk test of the present invention.

In FIG. 1A this activity is part of the block diagram 100 at block 1005 and a part of the two part Timed Walk aggregated activity as shown at block 104 of FIG. 1A. The mobile App displays an instruction page at screen shot 1005A on FIG. 7 that instructs the user to hold their mobile device steady in their hand and to take 25 steps. The user first clicks on a start icon 1005A1 to initiate the activity. The first time the user does this activity, he is asked to enter his height at input box 1005A3 which the app records which is used to calculate the distance walked. Once the activity is started, the mobile App displays an animation of a walking boy 1005A4 that continues until the activity is stopped. The App monitors changes in the values of the device accelerometer and magnetic sensor to determine when a new step is taken. The mobile App records a new event each time a new step is detected and ends with the user completing 25 steps and activating stop button 1005A2. This event represents the step that was taken and the and the time from the previous event to the current event in milliseconds (ms).

Activity 6: Coded Message Cognitive Test

Figure 8A:
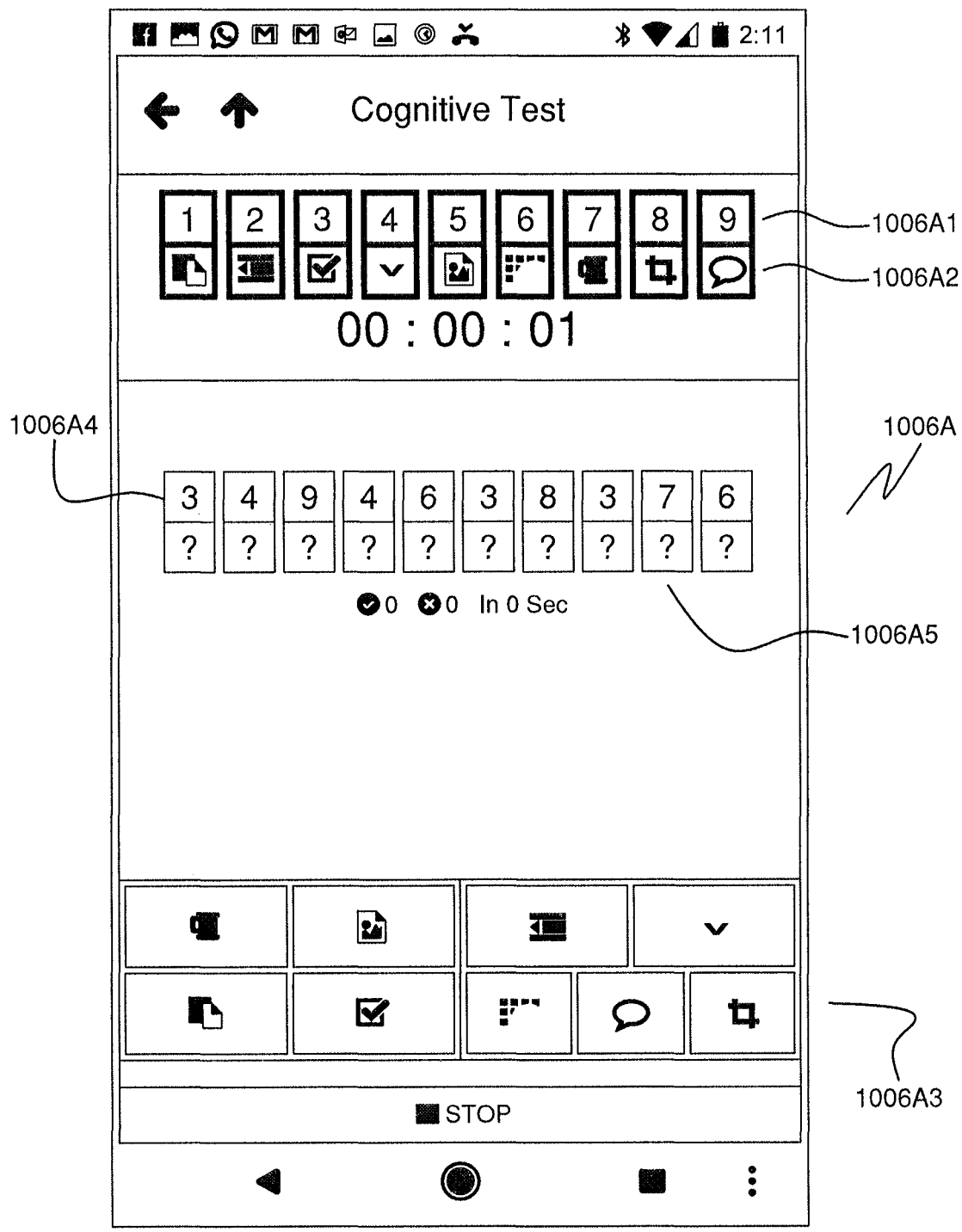
FIGS. 8A, 8B, and 8C illustrate the user's view of the screen of the application in connection with the Coded Message Cognitive test of the present invention.
Figure 8B:
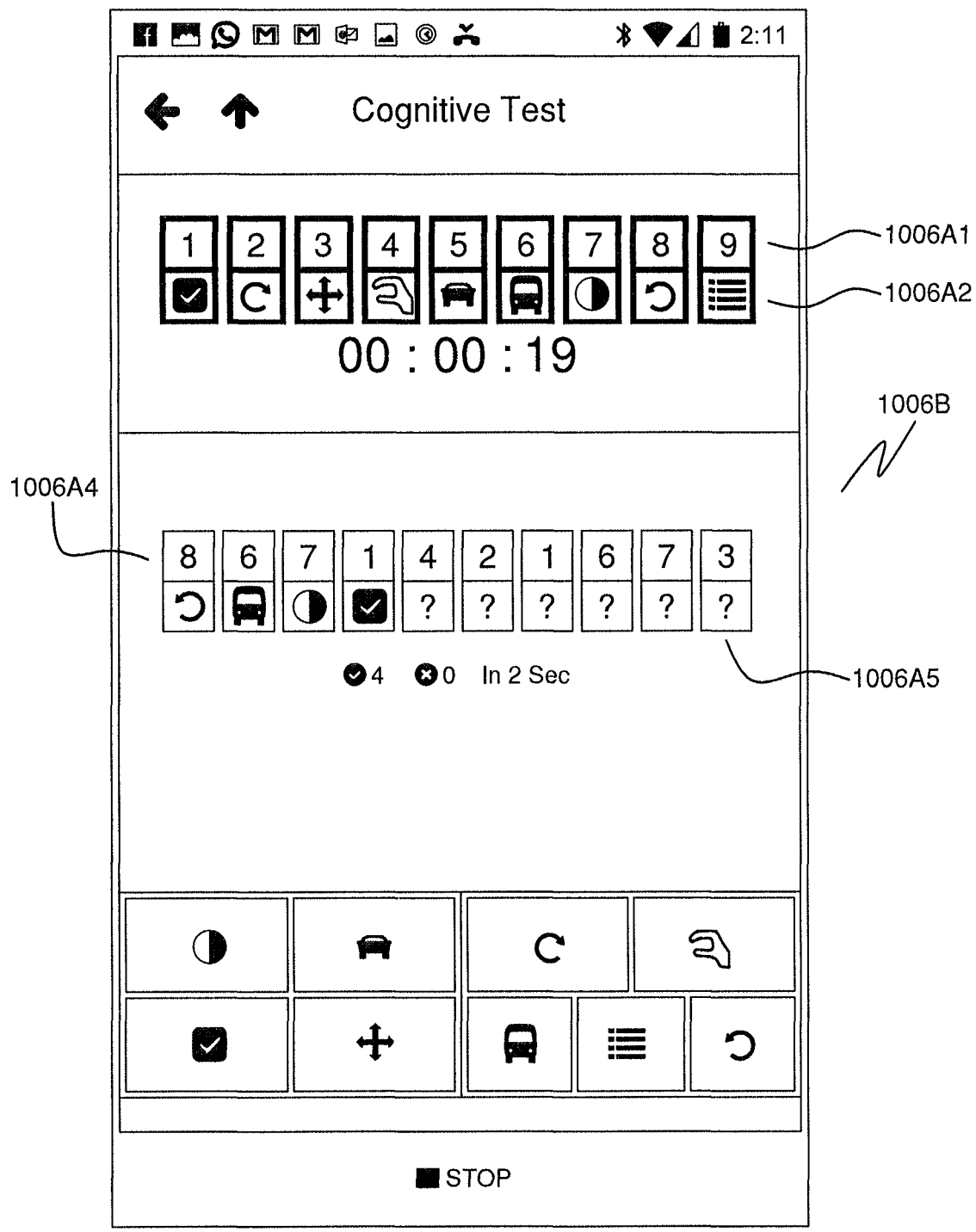
Figure 8C:
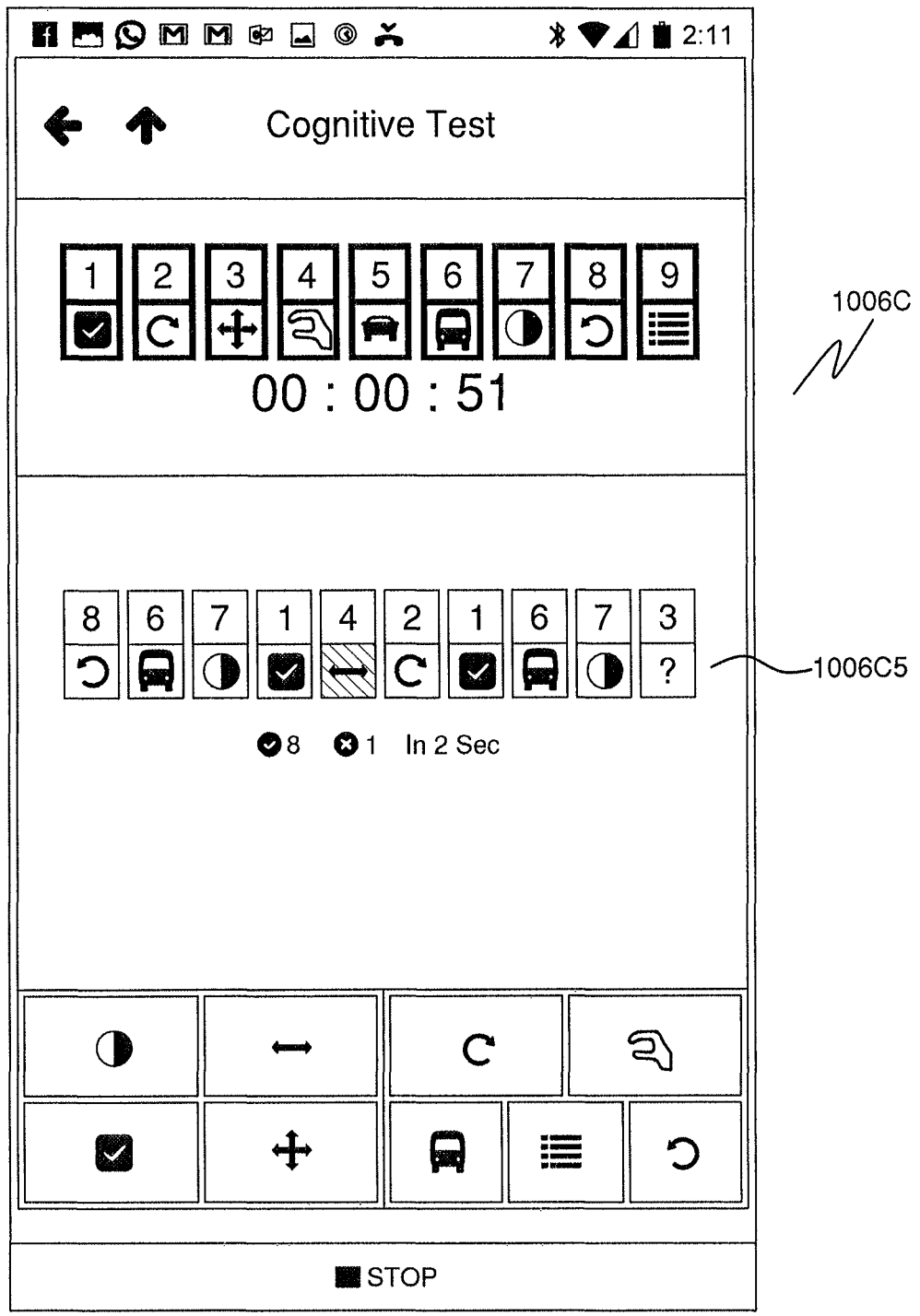

In FIG. 1A this activity is part of the block diagram 100 at block 1006. The mobile App first displays on screen display 1006A of FIG. 8A two rows of nine boxes in which the boxes in each row are aligned. Each box in the first row 1006A1 contains a single digit from 1 to 9. Each box in the second row 1006A2 contains a random, arbitrary symbol. Each symbol in 1006A2 directly below each digit in 1006A1 is to be considered by the user/patient to be an encoding of the corresponding digit. The mobile app gives the user 20 seconds to learn the association between the symbols and the digits, and then displays two additional rows of boxes in the middle of the screen at 1006A4 and 1006A5 along with a keyboard 1006A6 of the applicable symbols at the bottom of the screen as shown in FIG. 8A. The third row of boxes 1006A4 has a random digit in each box and the fourth row of boxes 1006A5 are initially blank. The user must choose the correct symbol from the virtual keyboard 1006A6 for each empty box in row 1006A5 that corresponds to the symbol in the box in row 1006A4 directly above. Each time the user presses a keyboard symbol in keyboard 1006A6, a state transition is recorded and the mobile App records a new event that represents the digit shown, the symbol chosen, the correct symbol, and the time from the previous event to the current event in milliseconds (ms). For example, screen display 1006B on FIG. 8B is show the user's progress after nineteen seconds have elapsed in attempting to match the numbers of 1006A4 with the proper symbols from 1006A2 by filling in row 1006A5. In FIG. 8B, all of the symbols placed below the digits were correctly mapped by the user/patient. In FIG. 8C, screen display 1006C shows additional progress by the user after fifty one seconds have elapse, but the shading of the symbol under the digit 4 shows that the wrong symbol was entered by the same user.

Activity 7: Six Minute Walk

Figure 9:
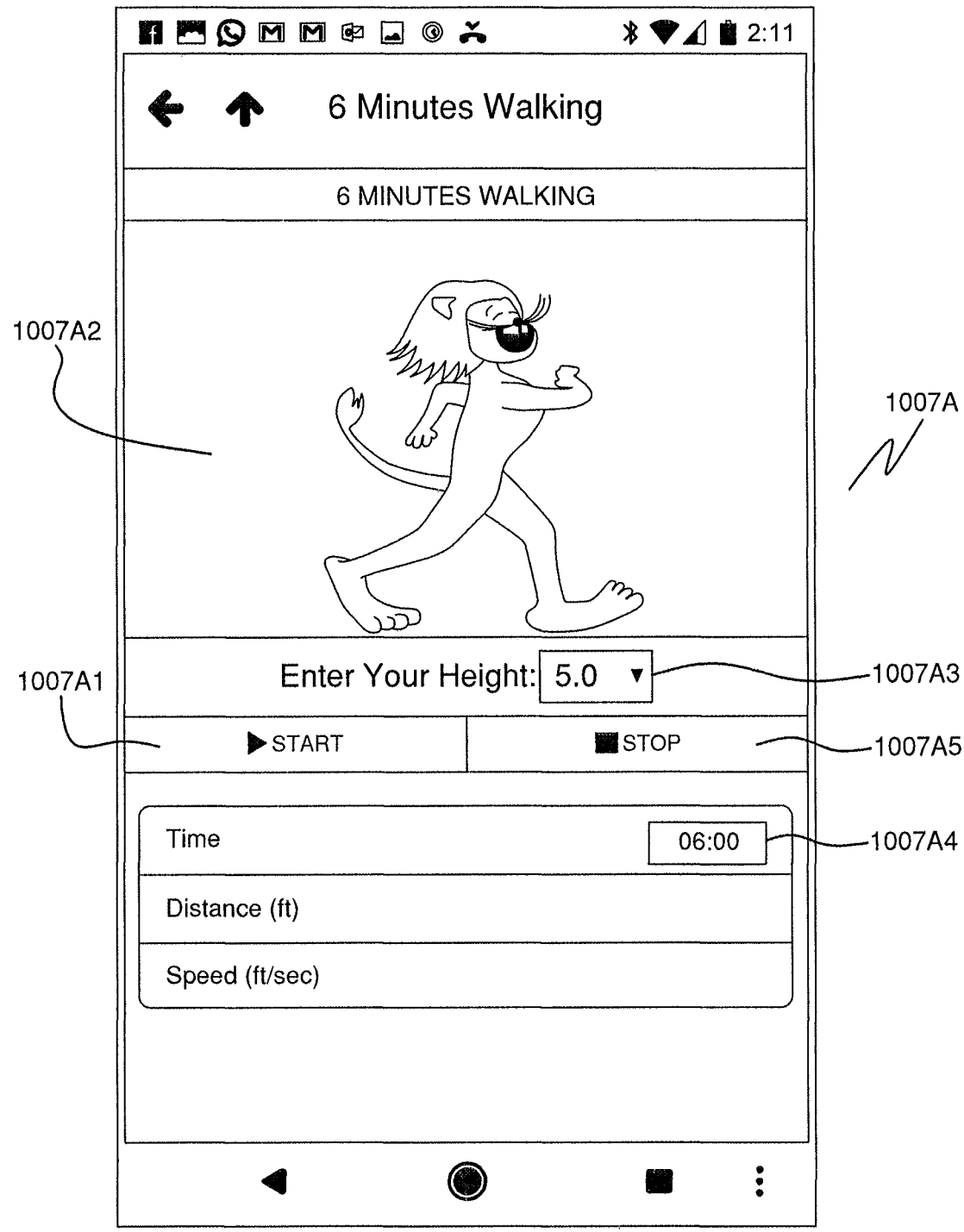
FIG. 9 is a representative screen shot from the 6 Minute Walk test of the present invention.

In FIG. 1A this activity is part of the block diagram 100 at block 1007 and a part of the two part Timed Walk aggregated activity as shown at block 104 of FIG. 1A. The mobile App displays an instruction page at screen shot 1007A on FIG. 9 that instructs the user to hold their mobile device steady in their hand and to walk at a comfortable and safe pace for 6 minutes. The user clicks on a start icon 1007A1 to initiate the activity. The first time the user does this test, he is asked to enter his height which the app records which is used to calculate the distance walked. The first time the user does this activity, he is asked to enter his height at input box 1007A3 which the app records which is used to calculate the distance walked. Once the test is started, the Mobile App displays an animation of a walking lion 1007A2 that continues until the test is stopped by the time as shown in 1007A4. The user can stop the test by clicking stop button 1007A5. The App monitors changes in the values of the device accelerometer and magnetic sensor to determine when a new step is taken. This event represents the step that was taken and the time from the previous event to the current event in milliseconds (ms).

Activity 8: Contrast Sensitivity Test

Figure 10A:
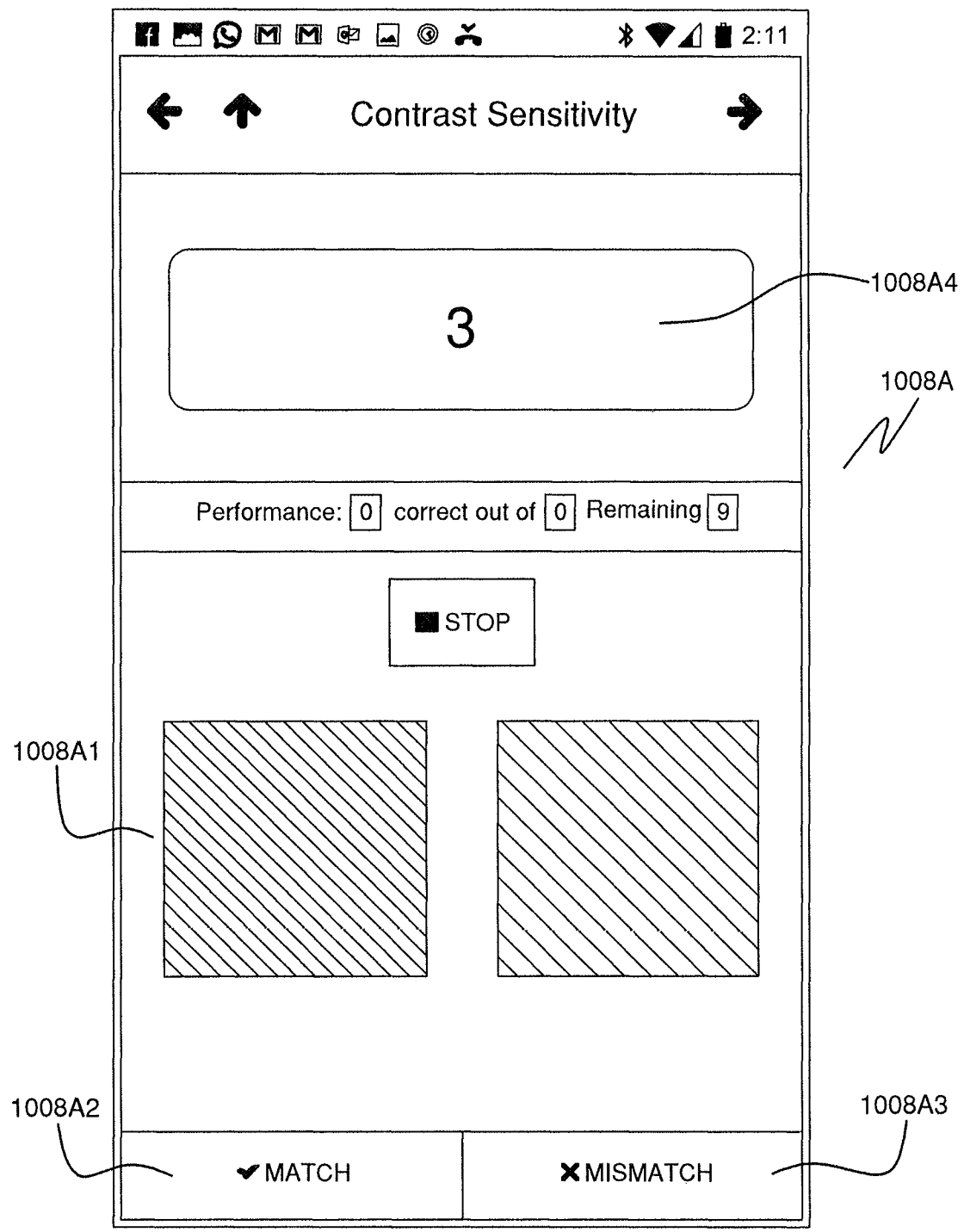
FIGS. 10A, 10B, 10C, 10D, and 10E illustrate the user's view of the screen of the application in connection with the Contrast Sensitivity test of the present invention.
Figure 10B:
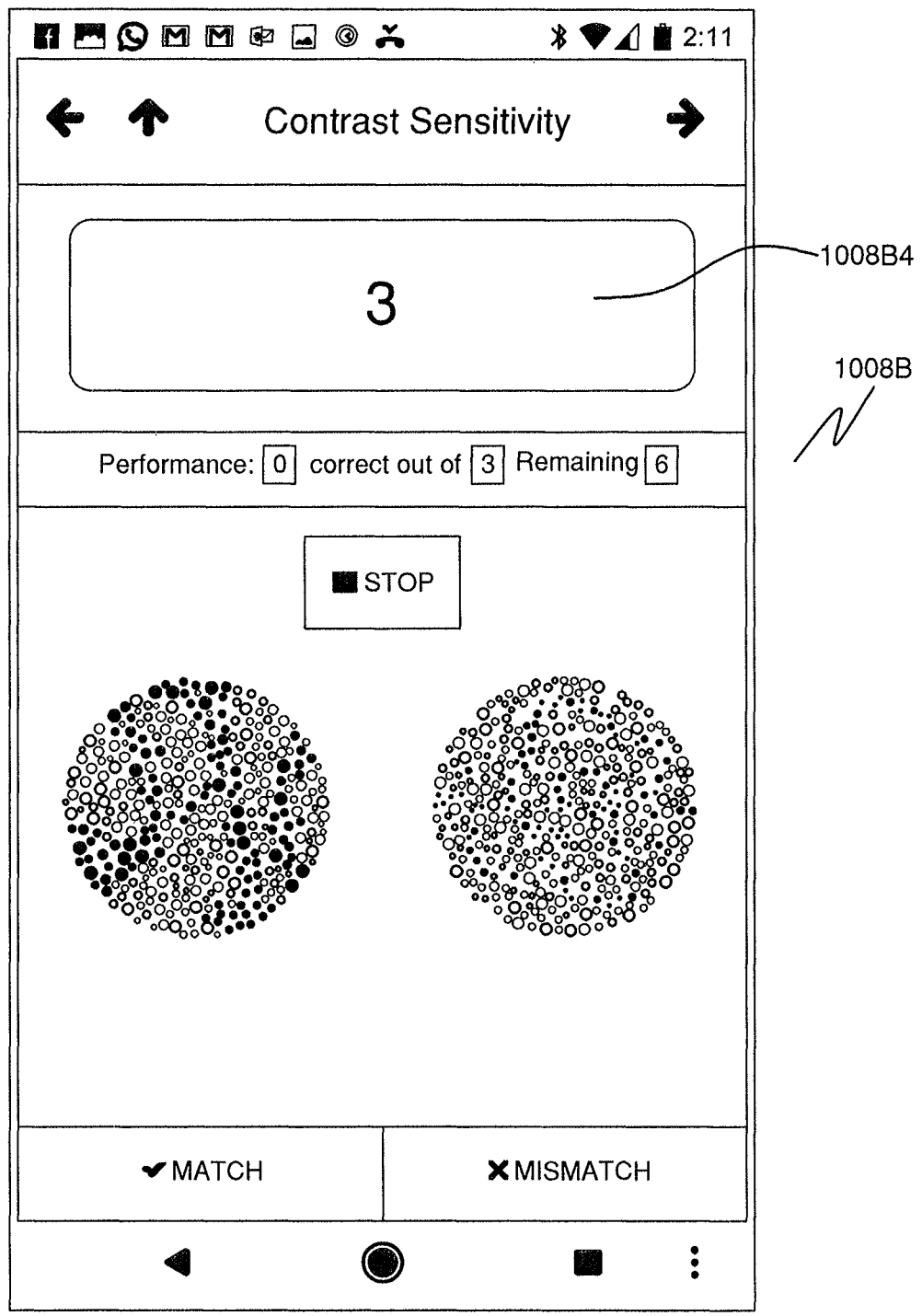
Figure 10C:
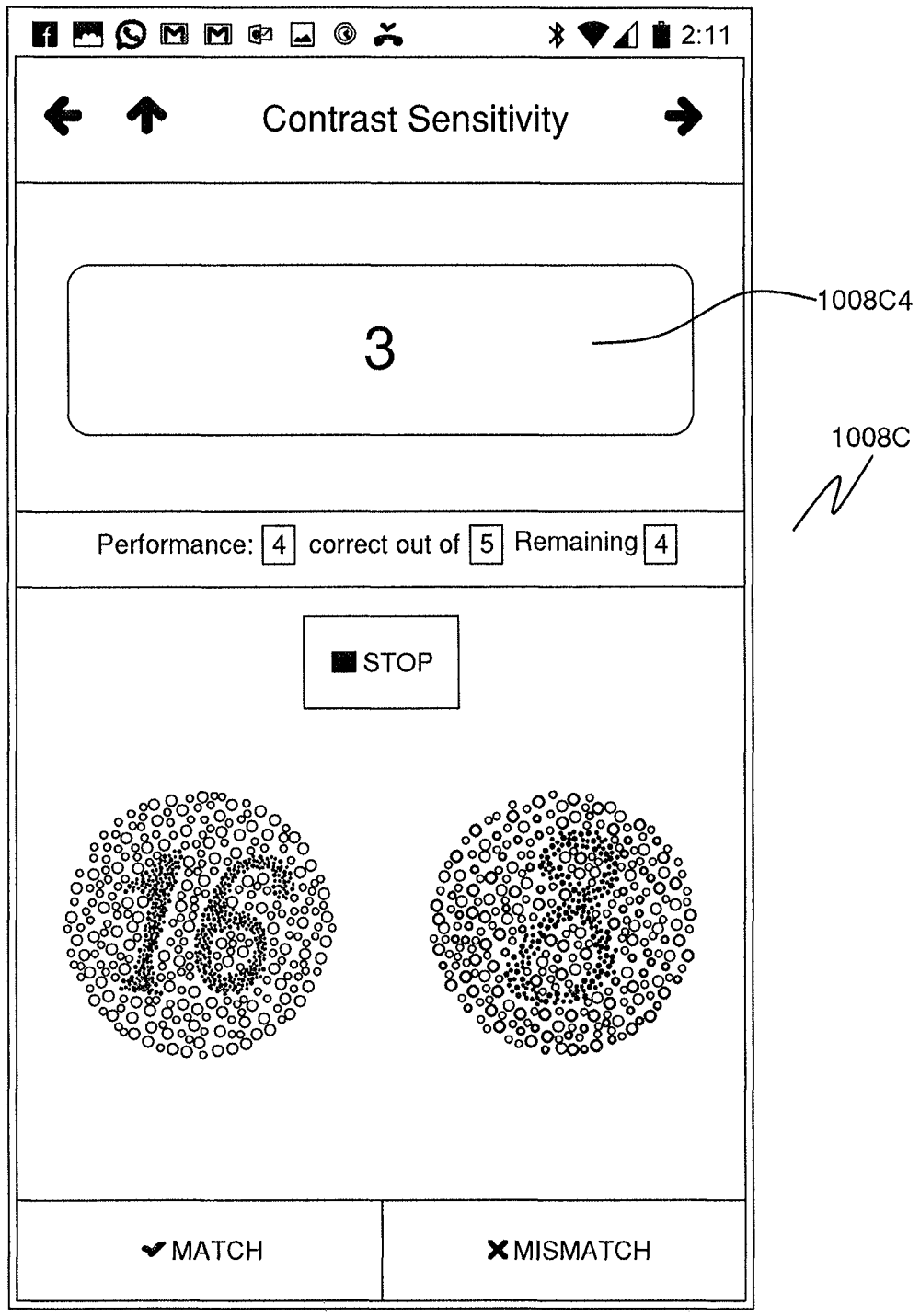
Figure 10D:
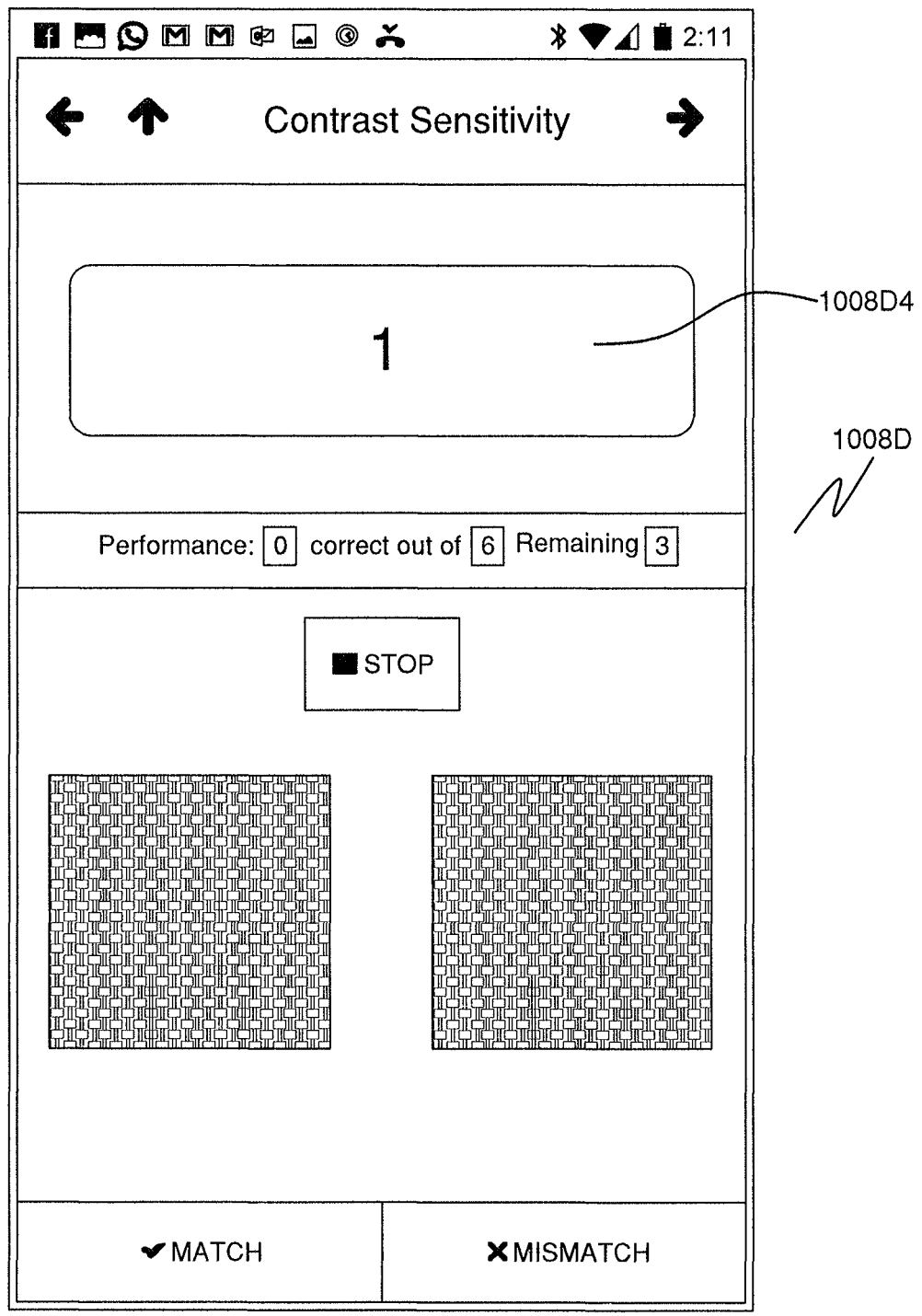
Figure 10E:
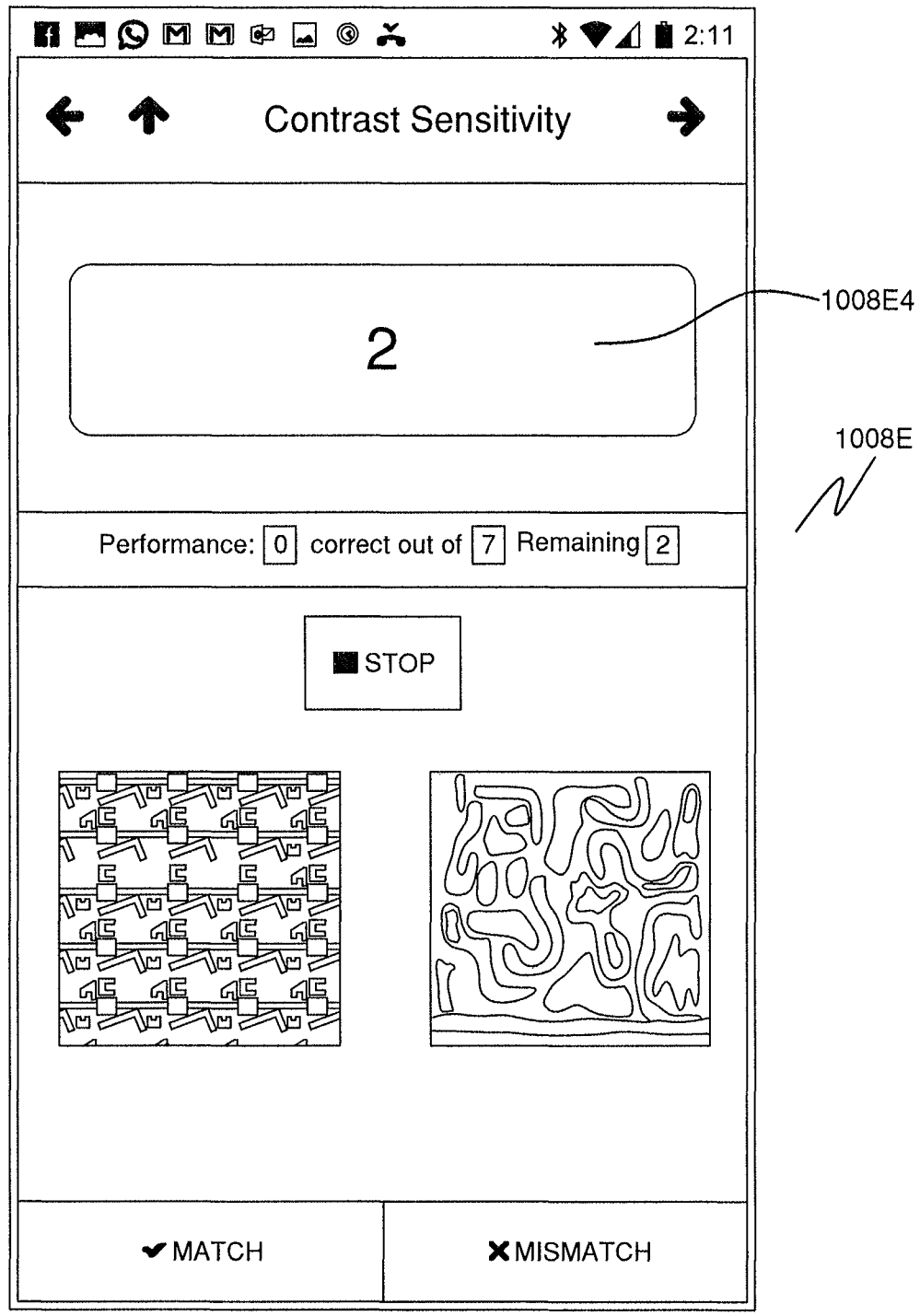
Figure 11:
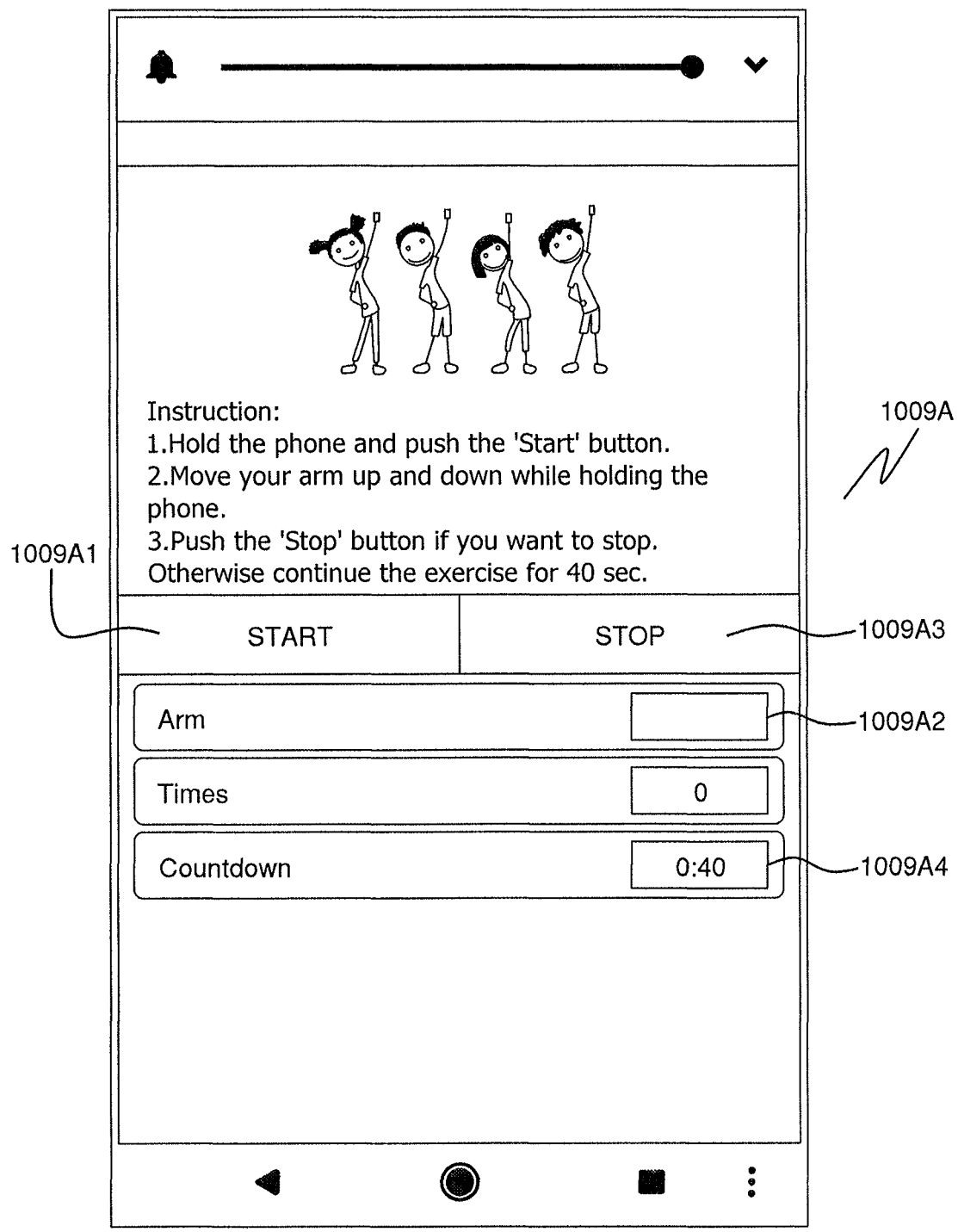
FIG. 11 is a representative screen shot from the Arm Swing test of the present invention.

In FIG. 1A this activity is part of the block diagram 100 at block 1008. The mobile App displays an instruction page at screen shot 1008A on FIG. 10A that instructs the user to mark a response as match if the two rectangular patterns that will displayed are the same, otherwise as mismatch. The user clicks on a start icon (not shown) to initiate the activity and has three seconds to complete each matching activity. The mobile App displays pairs of rectangular patterns 100A1 and two virtual buttons marked Match 1008A2 and Mismatch 1008A3 that the user will press to record his decision of whether the patterns match. The mobile App records a new event each time the user presses one of the two buttons 1008A2 or 1008A3 or after the time limit of three seconds has elapsed as shown by the countdown counter on each screen display 1008A, 1008B, 1008C, 1008D, and 1008E (respectively, 1008A4, 1008B4, 1008C4, 1008D4, and 1008E4, which show three, three, three, one, and two seconds remaining on the respective countdown counter respectively). This event records each pattern shown, whether the patterns match, and which button the user pressed and the time in milliseconds (ms) between the patterns appearing on the screen and the user pressing one of the buttons. In the order of FIGS. 10B, 10C, 10D, and 10E, the progress of the user is shown on each of the respective screen displays 1008B, 1008C, 1008D, and 1008E. Activity 9: Arm Swing Test In FIG. 1A this activity is part of the block diagram 100 at block 1009. The mobile App displays an instruction page at screen shot 1009A on FIG. 11 that instructs the user to hold their mobile device steady in their hand and to swing their arm holding the phone up and down for 40 seconds. The user clicks on a start icon 1009A1 to initiate the activity. The App monitors changes in the values of the device accelerometer and the gyroscope sensors to determine a change in the current direction of motion. The App displays a yellow rectangle 1009A2 when the phone is either stopped or moving in a constant direction. By reading changes in the values produced by the accelerometer, the App can determine whether the phone is continuing its current motion or not. by reading changes in the gyroscope when the value of the accelerometer is decreasing the App can determine when the mobile device 200 has reached its highest point or lowest point of elevation. When the App determines that the highest (lowest) elevation point was reached, it records a new Up (Down) arm event and turns the yellow box 1009A2 green. The mobile App records a new event each time a new high elevation or low elevation is detected. This event represents the time that was taken from the previous event to the current event in milliseconds (ms) and the type of arm motion (Up or Down). The user can stop the activity prematurely by clicking on the stop button 1009A3; otherwise the app will terminate the activity at 40 seconds as shown on the countdown screen 1009A4.

Activity 10: Color Determination Test

Figure 12A:
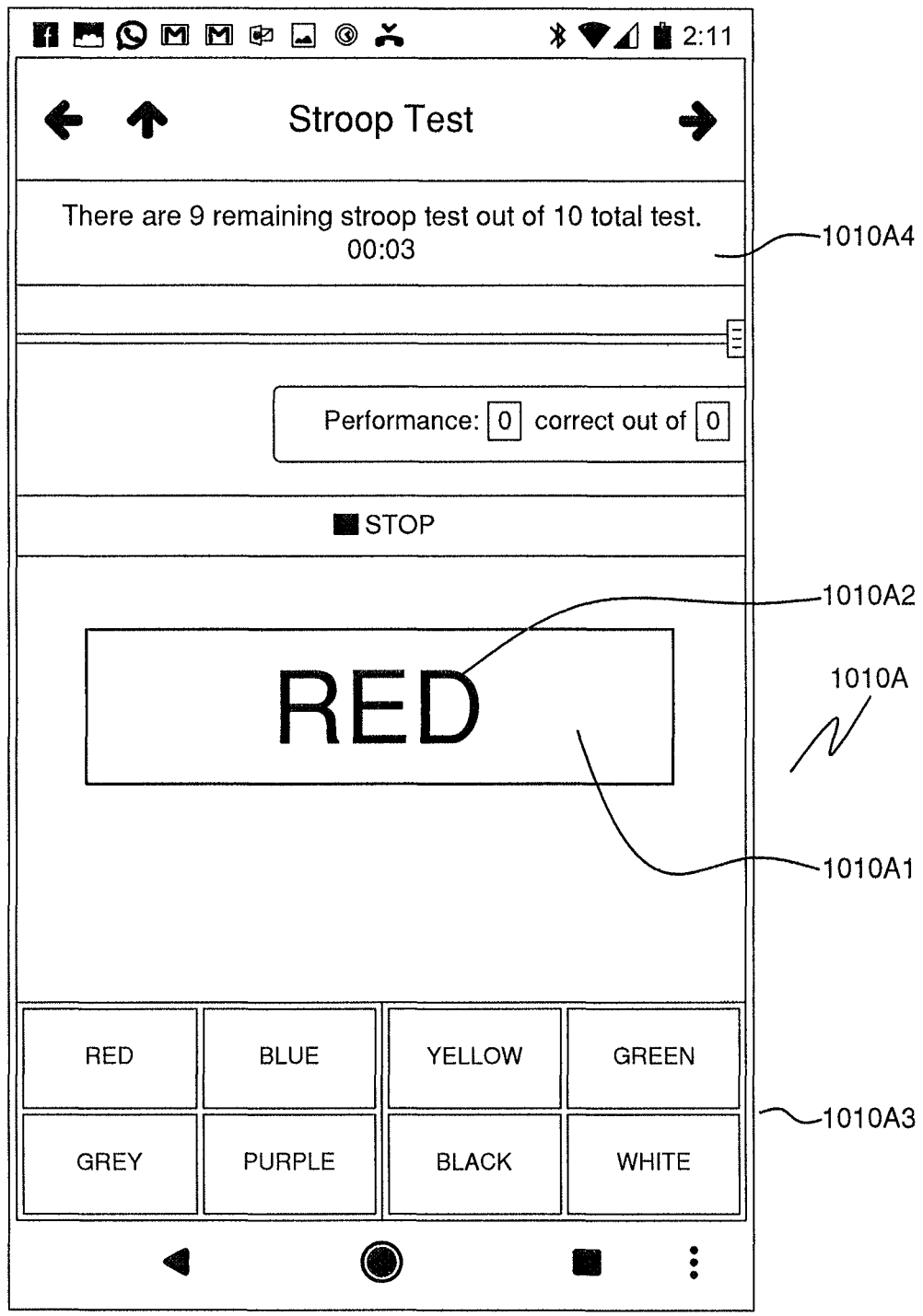
FIGS. 12A, 12B, 12C, 12D, and 12E illustrate the user's view of the screen of the application in connection with the Color Determination test of the present invention.
Figure 12B:
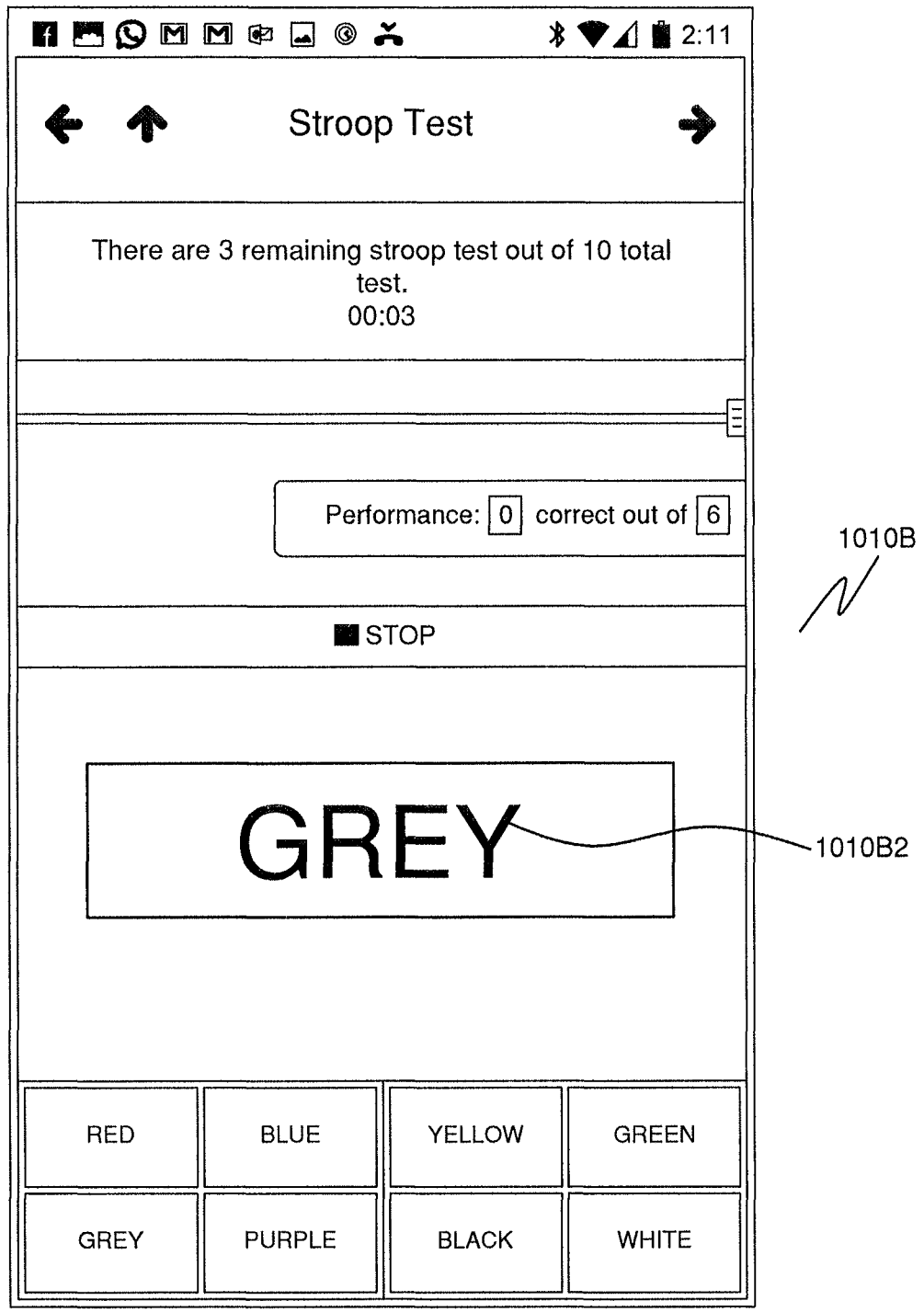
Figure 12C:
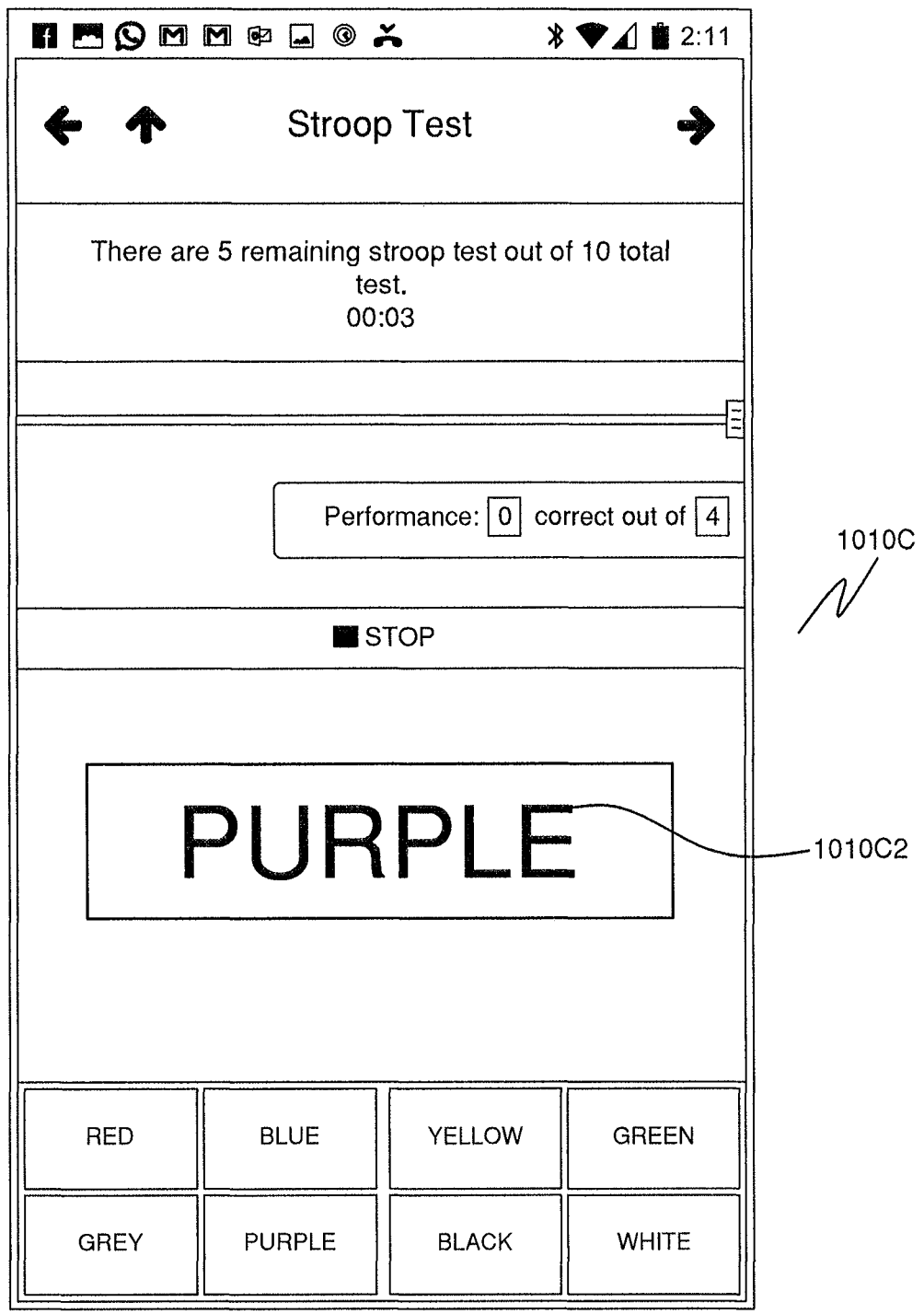
Figure 12D:
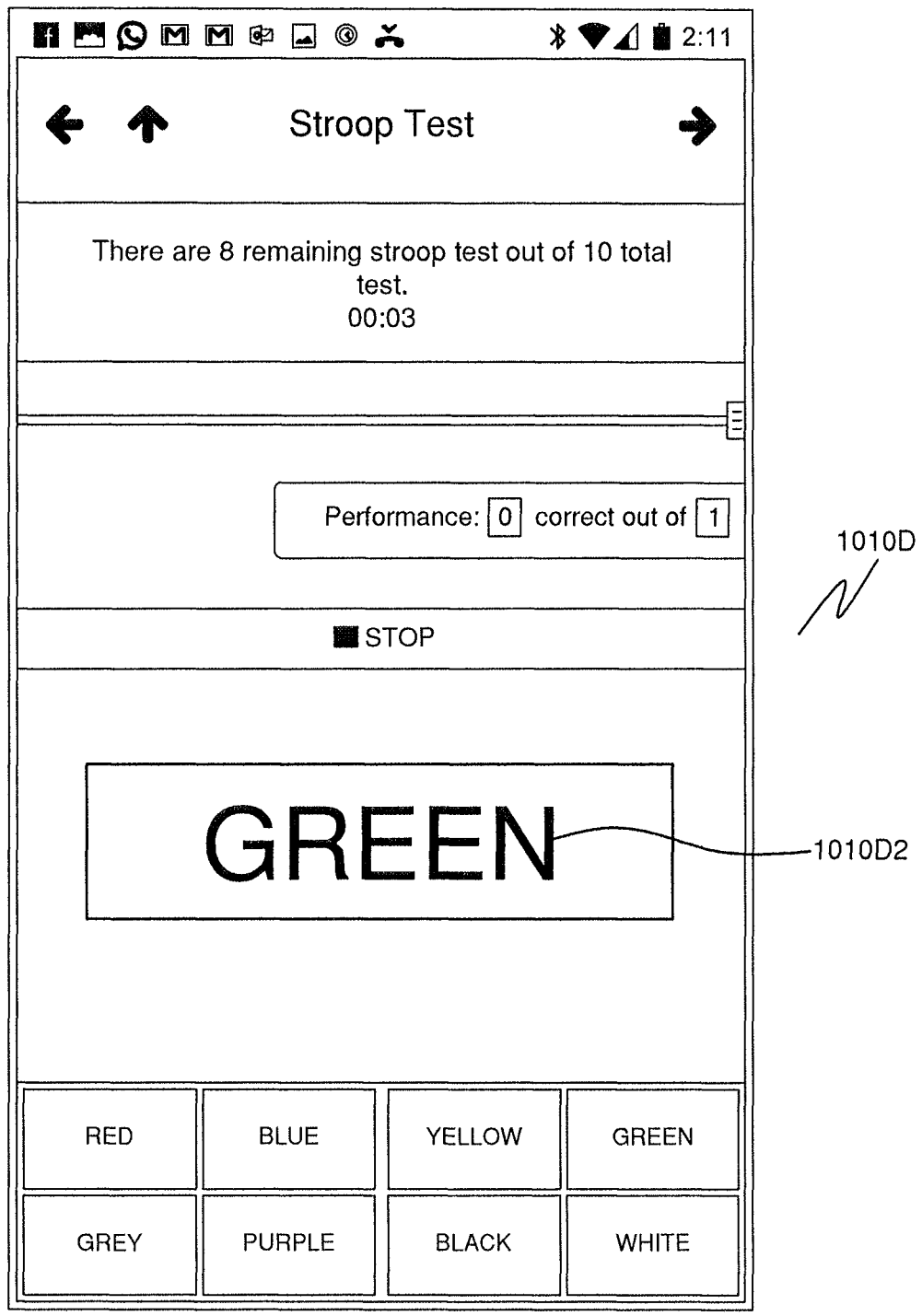
Figure 12E:
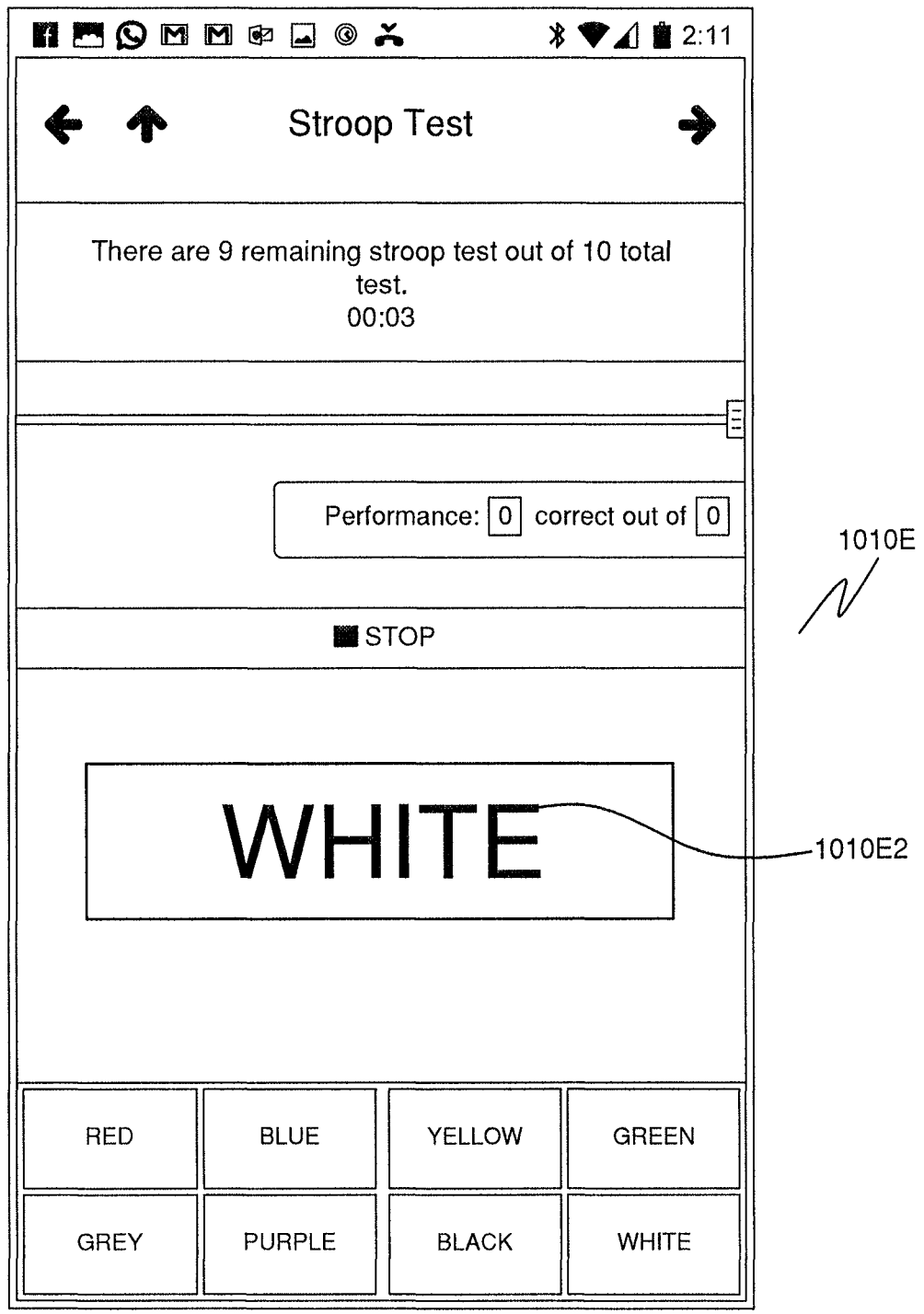

In FIG. 1A this activity is part of the block diagram 100 at block 1010. The mobile App displays an instruction page at screen shot 1010A on FIG. 12A that instructs the user to match the color of the text that is displayed in the grey rectangle 1010A1 of said screen display. There is a three second countdown from the time that screen display 1010A appears to the user after which a grey rectangle 1010A1 is displayed containing text 1010A2 corresponding to the name of a color, in the case of FIG. 12A the color named is RED. The text will appear in a different color, that is, in the case of FIG. 12A the color of the text may be, for example, blue, or any color other than red. The user has up to three seconds to hit a button on the keyboard 101A3 that fills the bottom of the screen display 1010A that is the same as the text 1010A2 color. The text that is displayed is purposely selected to distract the user from naming the correct color. The correct choice for the text color in the example presented is BLUE. The mobile App records a new event each time the user presses one of the eight buttons named with a color or if the 3 second timer 1010A4 has counted to zero. This event records the text and color shown, which color button was pressed by the user whether the choice was correct, and the time in milliseconds (ms) between the countdown starting and a color button chosen, or the timer going off. FIG. 12B, FIG. 12C, FIG. 12D, and FIG. 12E, respectively, show different examples of text having color of text differing from the word presented, specifically, in FIG. 12B the text GREY 1010B2 is green; in FIG. 12C the text PURPLE 1010C2 is grey; in FIG. 12D the text GREEN 1010D2 is red; and in FIG. 12E the text WHITE 1010E2 is yellow.

Activity 11: Animals in a Box Activity

Figure 13A:
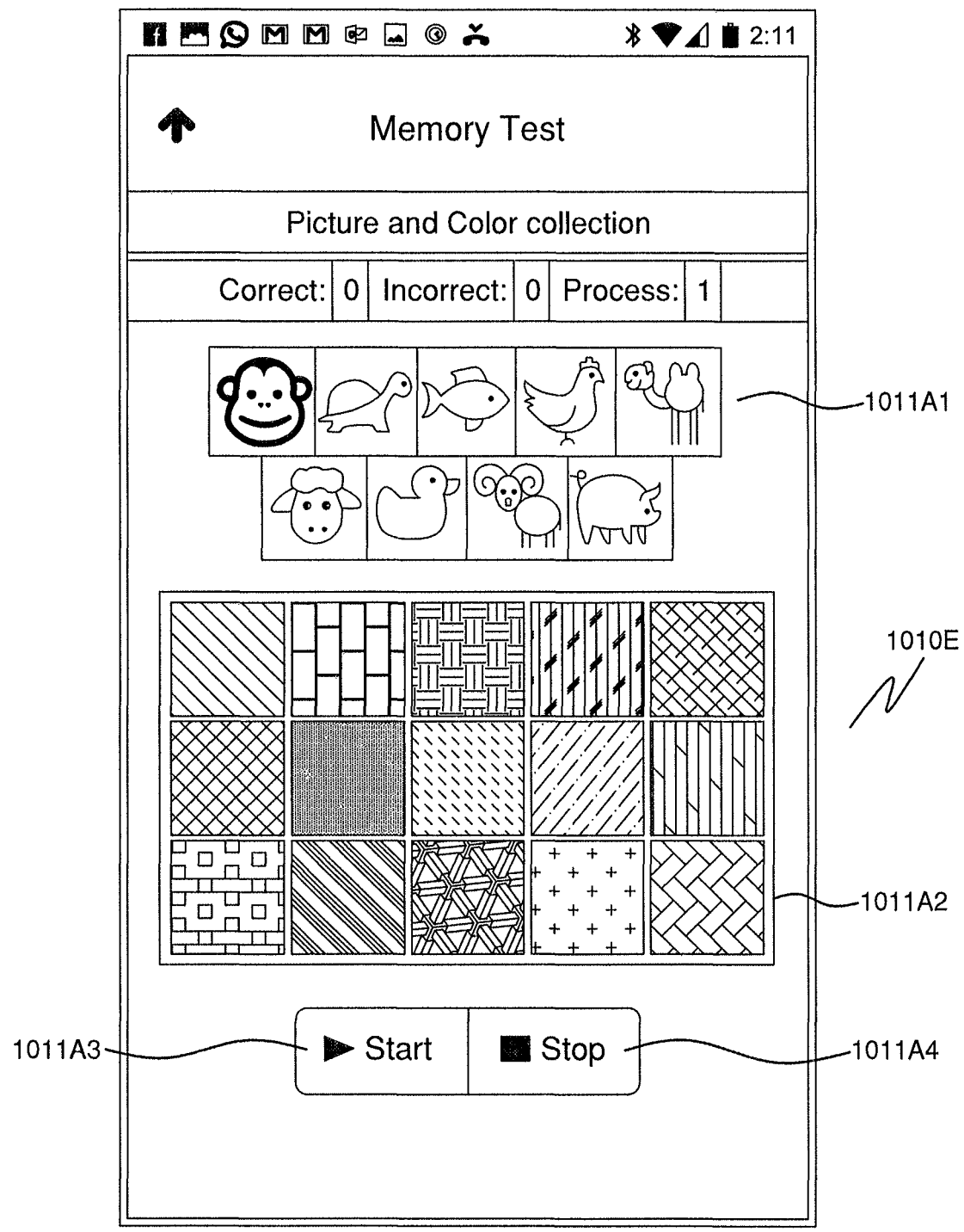
FIGS. 13A, 13B, 13C, and 13D illustrate the user's view of the screen of the application in connection with the Animals in a Box test of the present invention.
Figure 13B:
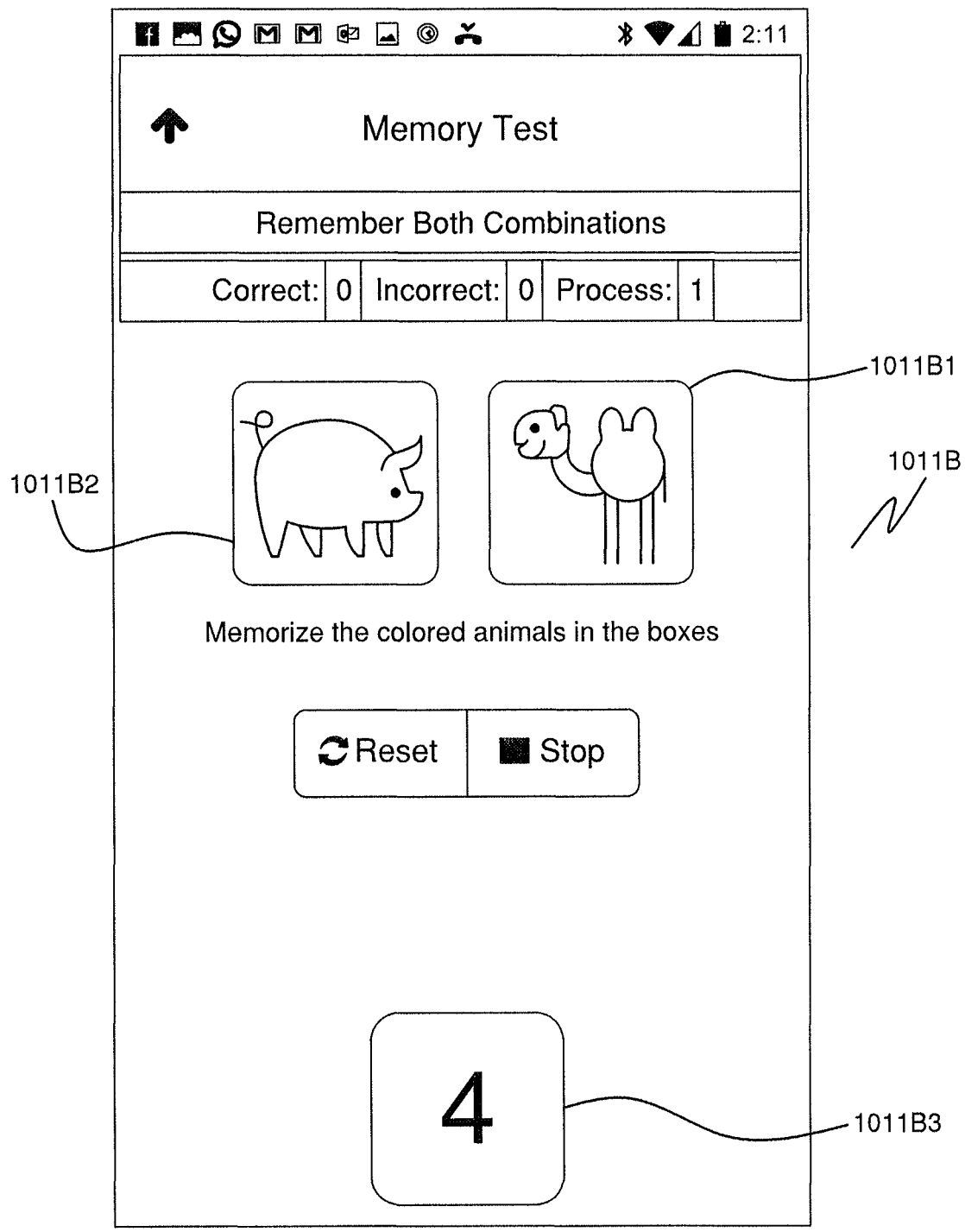
Figure 13C:
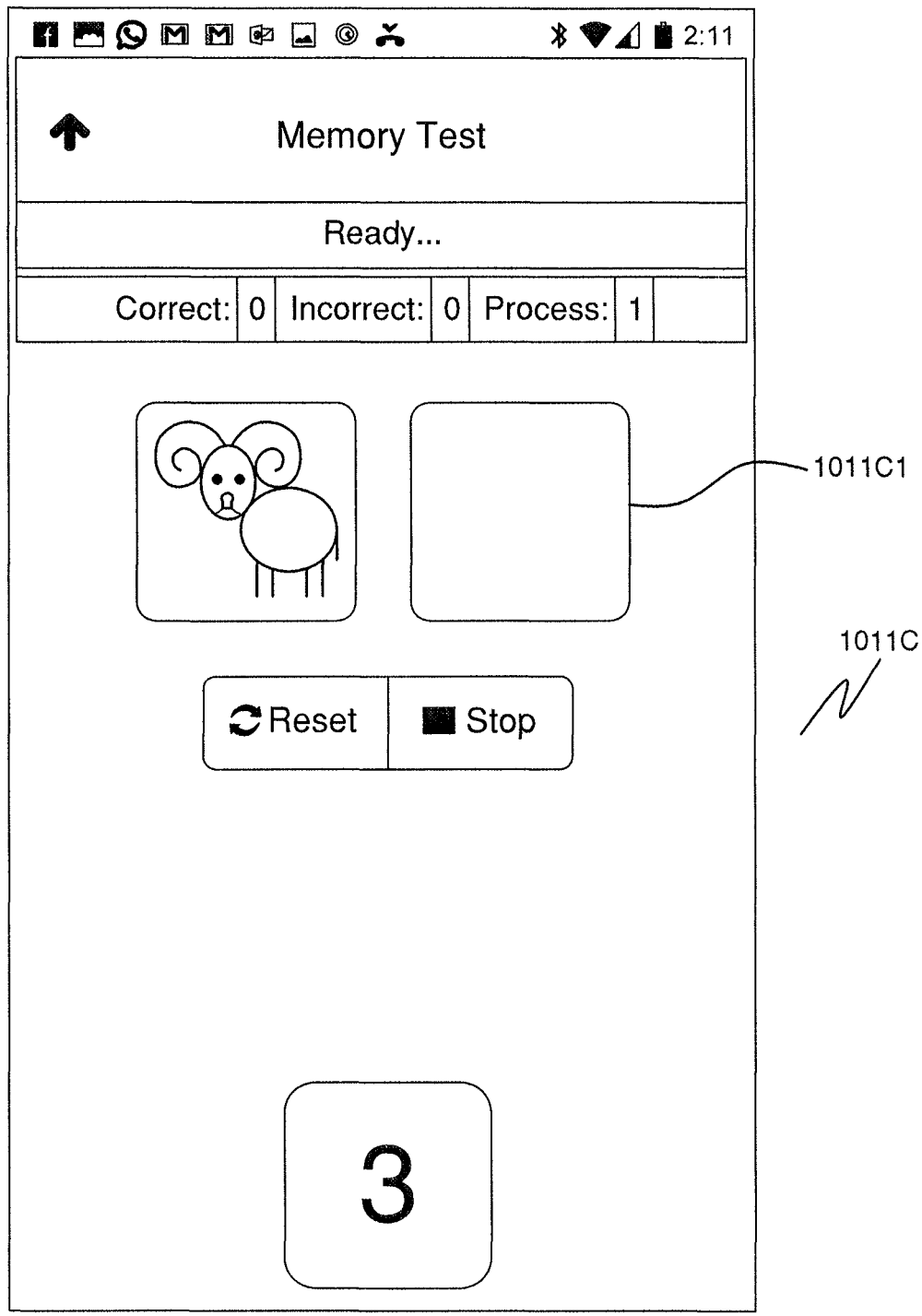
Figure 13D:
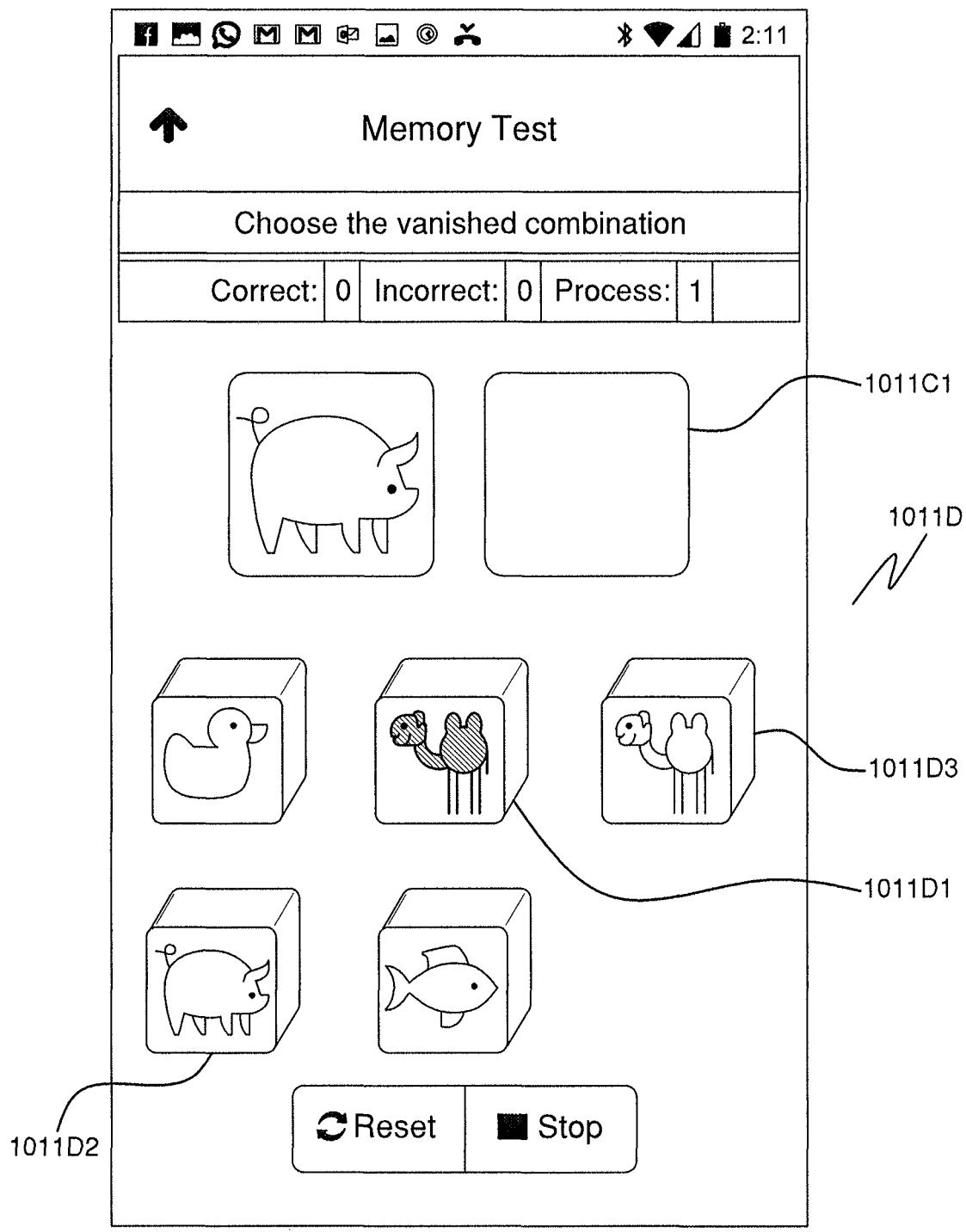

In FIG. 1A this activity is part of the block diagram 100 at block 1011. The mobile App first displays an instruction page at screen shot 1011A on FIG. 13A that presents the user that with two rows of animal icons 1011A1 and a set of colors 1011A2. This activity will measure the users ability to remember a recently displayed (animal, color) pair and a previously displayed (animal, color) pair. When the user presses the start button 1011A3 a second screen display 101B in FIG. 13B appears that initially displays two boxes 1011B1 (a blue camel) and 1011B2 (a red pig), with each box containing a different (animal color) combination. After a 5 second countdown as shown in countdown window 1011B3, screen display 1011C appears as in FIG. 13C in which one of the two boxes 1011C1 has been randomly blanked out and the user must choose which (animal color pair) is no longer displayed from a selection of choices in new screen display 1011D as shown in FIG. 13D. Those choices include only correct answer (in this exemplar, the blue camel of box 1011D1 as shown in screen display 1011D), and the incorrect choices include at least one other pair with the correct color (such as box 1011D2 with its blue pig), and one other paid with the correct animal and incorrect color (such as box 1011D3 with its grey camel). After making an choice, the box that was not blanked out is now blanked out, so that the user must remember the previous choice for the next time the test is run. The mobile App records a new event each time the user selects a choice. This event records the animal and color shown, the animal and color selected by the user whether the choice was correct, and time in milliseconds (ms) from the countdown starting until a choice is made.

Figure 14A:
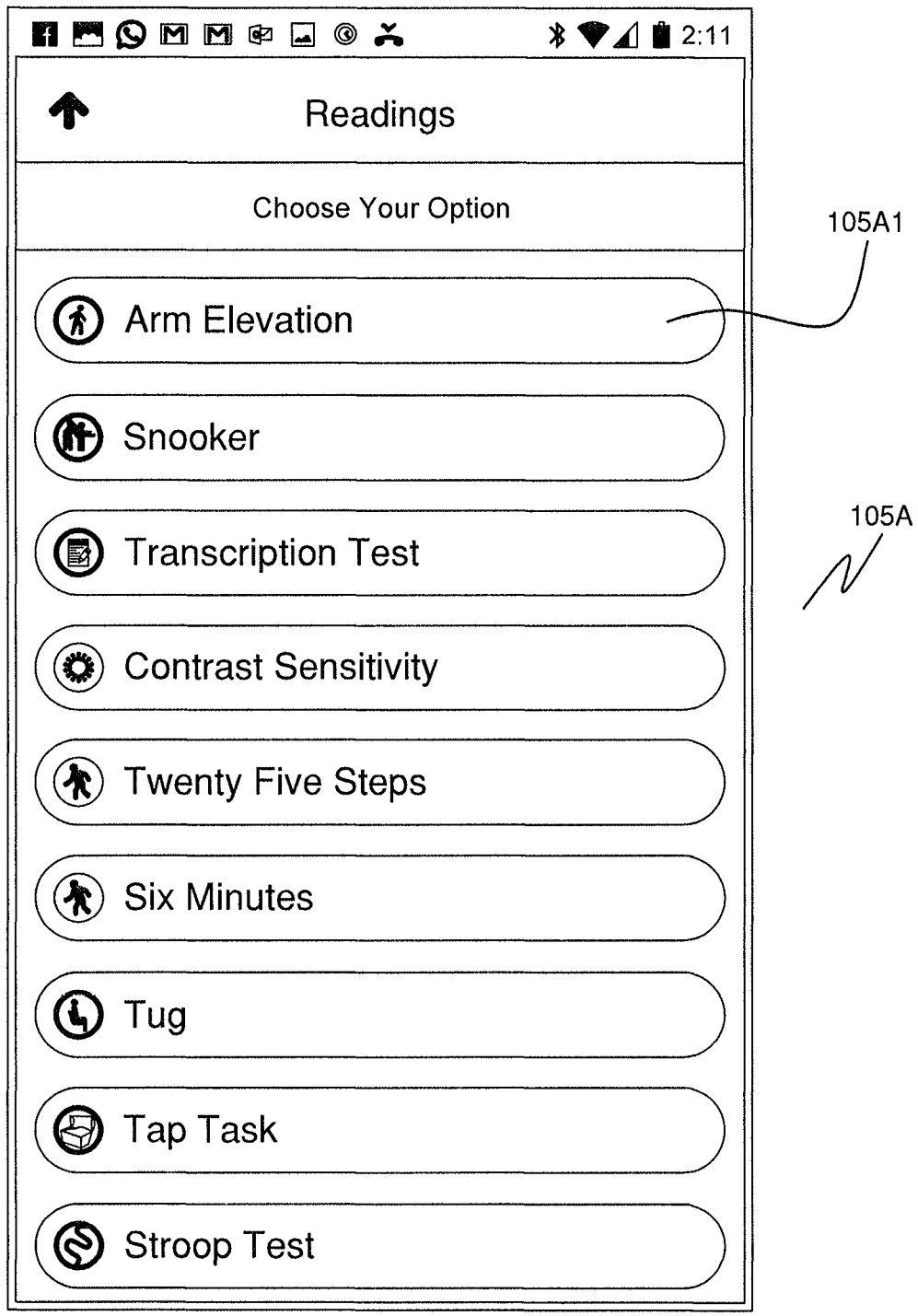
FIGS. 14A, 14B, and 14C illustrate the user's view of the review screens of the application of the present invention.
Figure 14B:
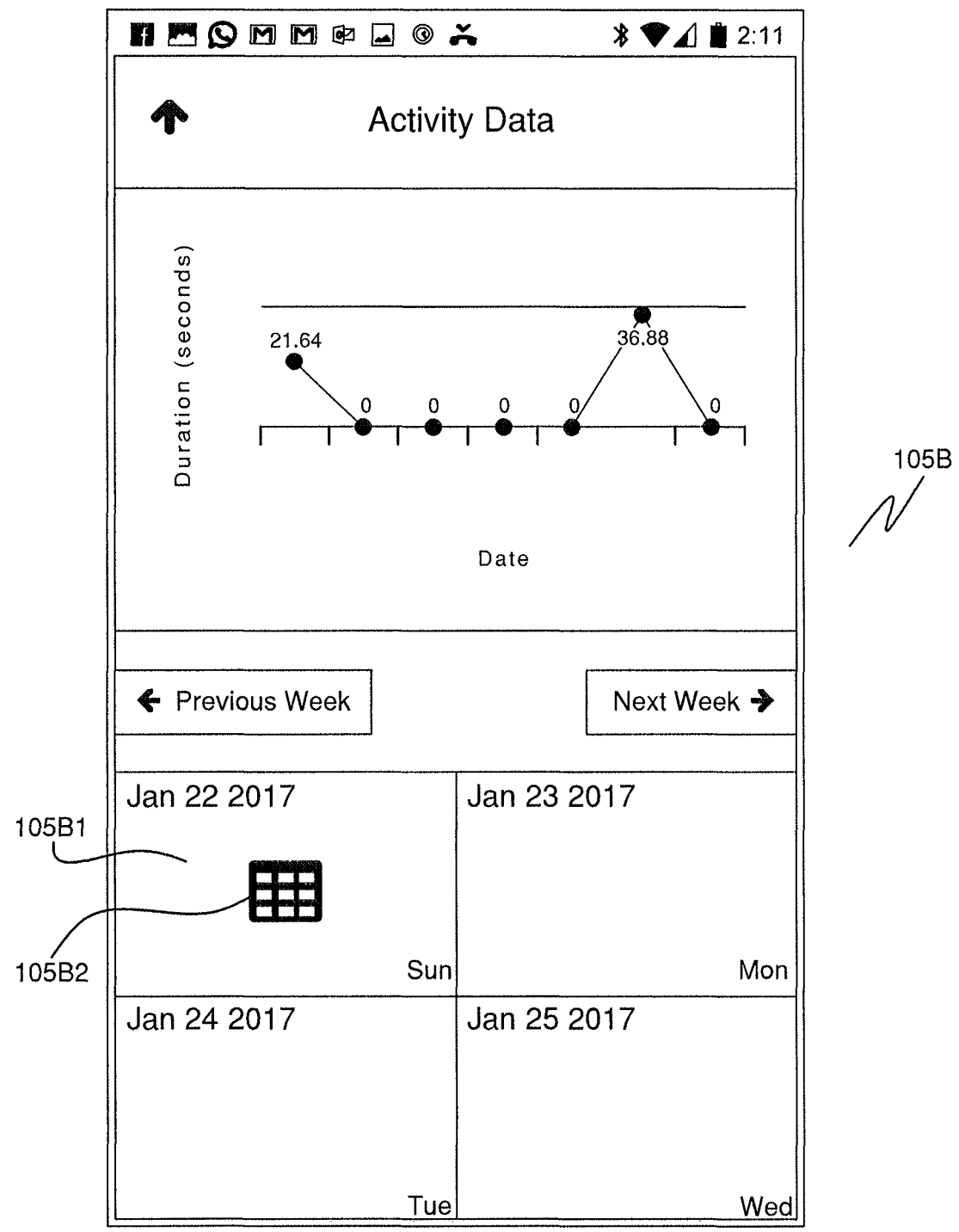
Figure 14C:
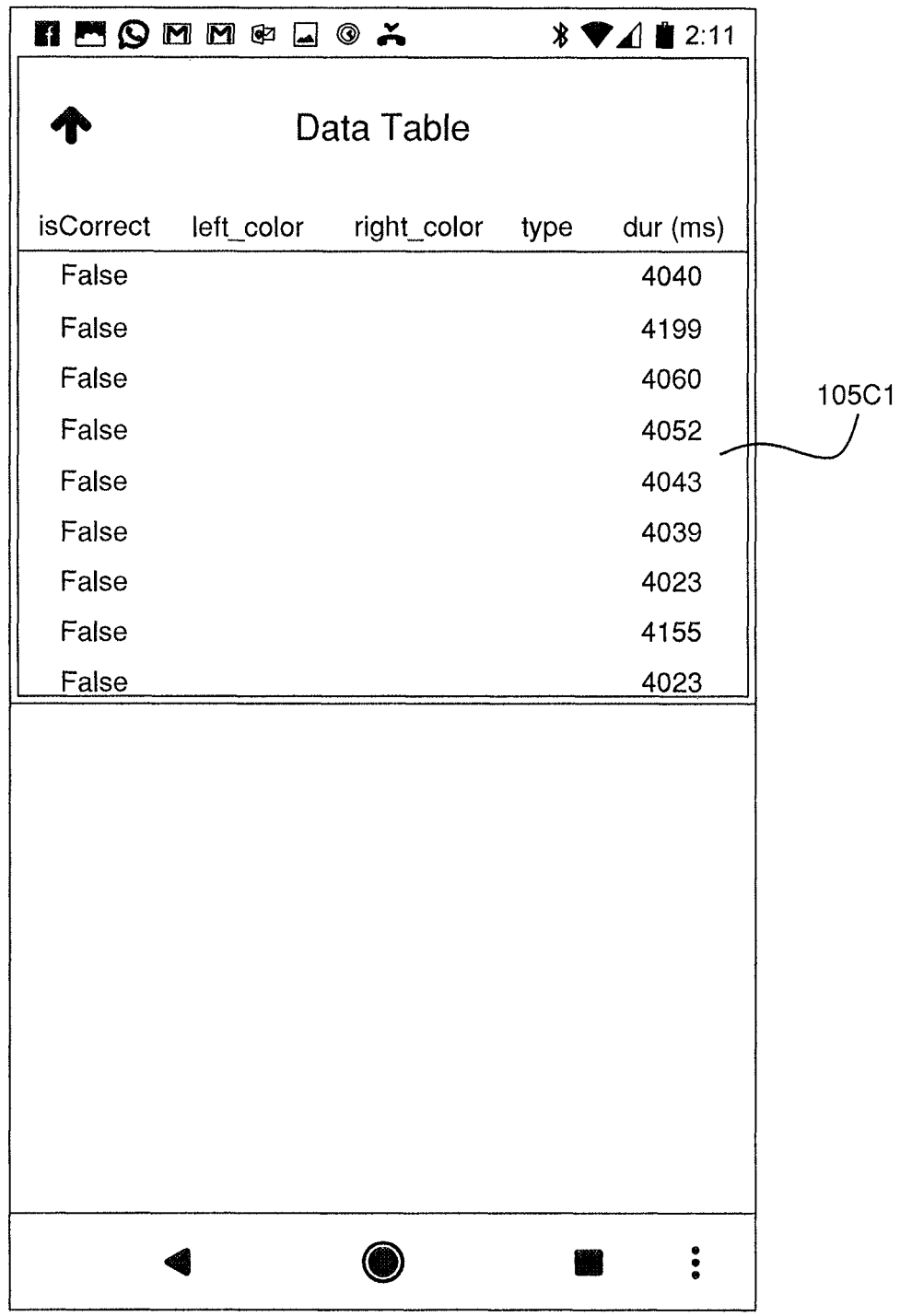

Before or after completion of the 11 activities, in the preferred embodiment the user can review his or her prior activity by selecting the Reading Review part of the application as shown as block 105 in FIG. 1A and by reviewing the screen display 105A as shown on FIG. 14A. On this screen display 105A the user is given a list of options that allow him to review his performance on each activity, such as, for example, his Arm Elevation Activity results by pressing touch screen key 105A1 on screen display 105A, over a particular date range. Selecting one of activity options allows the user to review his historical activity, such as that shown on screen display 105B on FIG. 14B. The activity graph shown thereon is a graph of the total daily time (in seconds) that the App recorded when the user performed this activity. A graph value of zero (o) indicates the user did not perform that activity on that day. Each non zero data point has a corresponding icon in the daily calendar that appears below the graph. When the user clicks on the a particular calendar on screen display 105B, for example calendar box 105B1 thereon, a rectangular area 105B2 is displayed with one or more identifiers that correspond to the number of times the user performed that activity on that day. By clicking on a particular identifier, the user can see his detailed performance for that activity as in the data table of screen display 105C1 on FIG. 14C.

The computer service referenced herein is a software implementation of different computer algorithms that run in a cloud computer environment 300 that analyze the event data such as that shown in screen display 105C1 that was generated by the mobile App. Additionally the computer service is responsible for implementing an encrypted communication facility between the mobile App running on mobile device 200 and the cloud environment 300 in FIG. 1B.

The computer service implements the encrypted data facility via the use of SSL technology. SSL (Secure Sockets Layer) is a standard security technology for establishing an encrypted link 400 in FIG. 1B between a server (in the cloud 300) and a client (the mobile device 200). As described previously, as the user completes the App activities, the App creates a sequence of software states that correspond to the actions that the user has performed. A representation of these states is first saved by the App in a private storage area provided by the mobile device operating system.

As described earlier, the user first logs into the App running on device 200 at block lot of FIG. 1A with a username and password to establish an authenticated session with the cloud facility 300. Once the user has been authenticated, the cloud service 300 maps the user to a unique identifier which will used to store and retrieve that user's data in the cloud database. The cloud database is a set of web-based services for running queries on structured data. After logging in to the mobile App at block 100, the user can perform the activities on the Wellness page at block 102 which will generate data to the App private storage area. Periodically the App will monitor the private storage area and if the private storage has at least one data item, the App will attempt to initiate an SSL connection 400 from the mobile device 200 to the designated cloud service 300. Once the connection has been successfully established, an encrypted representation of the data in the private mobile storage area is transferred from the mobile device 200 to the cloud service 300 (called a push operation) via encrypted link 400. After the App generated data has been pushed from the mobile device 200 to the cloud 300, the data in the private storage area is deleted.

Once the user's data has been successfully stored in the cloud database 300, the cloud service can analyze that data using certain machine learning algorithms (MLAs). An MLA is an algorithm that can produce classifications of data by being trained on a dataset called a "training set". The training set consists of data that was generated by a mobile App user while performing the mobile activities tasks, and associating that data with the corresponding EDSS scores assigned by a trained professional. In a process known as "training", the algorithm solves a sequence of optimization problems to produce a function that 1) assigns a score to each of the training examples that is reasonably close to the known score; and 2) assigns reasonable scores to patients whose true scores are not yet known. That is, the output of the SVM is a function that performs well on the training set and generalizes well to unseen observations. In practice, the algorithm is trained with data obtained from a clinical trial in which the MLA has access to both patients' performance on the application's tasks and their EDSS scores.

In the current implementation of the preferred embodiment, the interface for extracting data from the cloud database 300 for use by the MLA is through specially formatted queries using the unique identifier for that user. The cloud database 300 will provide particular user activity data using a standard software representation called the JSN representation. An example of a particular item of data corresponding to the Transcription Test returned to the MLA is:
{activityname=Transcription Test, seq=3, value={"orig_char":K, "user_char":K}, dur (ms)=3638, time=20161108 15:29:56}

Next, a program written in C # goes through this text file and collects statistics about the patient's performance in a process known as "feature extraction". For example, the feature extractor counts how many times the patient entered a character that matched the corresponding character in a given message in the Transcription Test activity. The proportion of correct entries is a statistic that we feed to the SVM and all such statistics are called "features." Several statistics for each activity are collected for a total of approximately two to three dozen features. One of the MLAs used to associate a patient's performance on the mobile App activities with an Expanded Disability Status Scale (EDSS) score is the Support Vector Machine (SVM), a commonly used machine learning algorithm (MLA). The SVM, implemented in C # using the Accord.NET library, is trained using known scores corresponding to the features extracted above. Specifically, the algorithm produces a set of weights that generate a nonlinear function of the input features. It accomplishes this by applying a nonlinear transformation, a Gaussian radial basis function in our case, to the input data and finding weights that minimize a loss function of the transformed data. This loss function penalizes choices of weights that either lead to poor predictions for the training data or produce an overly complicated model. The weights that minimize the loss function are found using a process implemented in the Accord library called Sequential Minimal Optimization. The result is a function that accurately assigns EDSS scores to the training data and generalizes well. How well the function generalizes is measured using cross validation. When a new patient/user completes the tasks in the mobile application, features are extracted from their performance data and then fed to the function output by the SVM which assigns an accurate EDSS score. A second MLA, implemented in C # that was specifically developed for this implementation is an artificial neural network (ANN). The ANN is a computing model where the computing nodes are organized in layers. Data is supplied to the input layer, and the hidden layers use a learning function to compute a representation of the data. In this implementation, the learning function that was used is backpropagation, which is a well known method for training an ANN. The output layer in our case is a score similar to the EDSS score.

The inputs to the ANN are derived from the user generated activity data that has been stored in the cloud database 300. The particular inputs are statistics that derived from the specific activity that the user performed. In the case of a cognitive activity, having a sequence of data items corresponding to the state transitions that the mobile App saved, the inputs are:
 1. the average time duration of the particular data items
 2. the standard deviation of the time of the particular data items
 3. the percentage of correct answers In the case of an mobile App activity having a variable number, or large number of repetitions such as the 6 Minute Walk Activity at block 1007 of FIG. 1A, the 25 Step Walk Activity at block 1005 of FIG. 1A, or the Arm Elevation Activity at block 1009 of FIG. 1A, the inputs to the ANN are:
 1. the average time duration of the particular data items
 2. the standard deviation of the time of the particular data items
 3. the number of steps In the case of the Timed Up and Go (TUG) activity at block 1001 of FIG. 1A, the inputs to the ANN are the 6 time duration intervals corresponding to the duration between the 6 successive states specified by the implementation.

As may be appreciated, the specification of the invention set forth herein relates in great part to the preferred embodiment of the invention, but other embodiments of the instant invention are also to be understood to be covered hereby.

What is claimed is:

1. A method for measuring with precision the disability status of a multiple sclerosis patient using a smartphone with an application program running thereon comprising the steps of:

logging into said program by said multiple sclerosis patient;

establishing a session on said program by said multiple sclerosis patient;

manipulating said smartphone by said multiple sclerosis patient in order to launch and perform a TUG activity, a fine motor function/rapid finger movement activity, a hand/eye activity, a transcription activity, a twenty-five step walk activity, a coding activity, a six minute walk activity, a color match activity, and a memory activity within said program;

detecting and recording precise timings of state transitions in said multiple sclerosis patient's manipulation of said smartphone by said smartphone; and storing said recorded precise timings in milliseconds in said smartphone by said smartphone;

wherein said precise timings recorded on said smartphone provide a precise measure of the multiple sclerosis disability status of said multiple sclerosis patient.

2. A hand held electronic device for measuring with precision the disability status of a multiple sclerosis patient consisting of:

a microprocessor;

a power supply;

a touch screen;

a memory in which is resident an application program for use by said multiple sclerosis patient comprising a log in program; a launch program; a wellness program that comprises a set of ordered activities to be performed by said multiple sclerosis patient, which said set of ordered activities comprise: a TUG activity, a fine motor function/rapid finger movement activity, a hand/eye activity, a transcription activity, a twenty-five step walk activity, a coding activity, a six minute walk activity, a color match activity, and a memory activity; and a reading review program;

an accelerometer;

a gyroscope; and a magnetic sensor, whereby said device detects, records, and stores precise timings in milliseconds of state transitions in said patient's manipulation of said device, which recorded precise timings in milliseconds provide a precise measure of the disability status of said patient.

* * * * *